US009220243B2

(12) United States Patent
Miller et al.

(10) Patent No.: US 9,220,243 B2
(45) Date of Patent: Dec. 29, 2015

(54) MODELS OF ATHEROSCLEROSIS, HYPERLIPIDEMIA, LIPOPROTEIN OXIDATION AND BLOOD VESSEL INFLAMMATION AND METHODS FOR MAKING AND USING THEM

(75) Inventors: Yury Miller, San Diego, CA (US); Konstantin Stoletov, San Diego, CA (US); Richard Klemke, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1615 days.

(21) Appl. No.: 12/445,283

(22) PCT Filed: Sep. 28, 2007

(86) PCT No.: PCT/US2007/079927
§ 371 (c)(1),
(2), (4) Date: Mar. 15, 2010

(87) PCT Pub. No.: WO2008/048773
PCT Pub. Date: Apr. 24, 2008

(65) Prior Publication Data
US 2010/0242123 A1    Sep. 23, 2010

Related U.S. Application Data

(60) Provisional application No. 60/851,516, filed on Oct. 13, 2006.

(51) Int. Cl.
G01N 33/00   (2006.01)
A01K 67/00   (2006.01)
A01K 67/027  (2006.01)
C12N 15/00   (2006.01)
C12N 5/00    (2006.01)
C07K 14/775  (2006.01)

(52) U.S. Cl.
CPC ........... A01K 67/0275 (2013.01); C07K 14/775 (2013.01); *A01K 2227/40* (2013.01); *A01K 2267/0362* (2013.01)

(58) Field of Classification Search
CPC .................... C07K 14/775; A01K 67/0275
USPC ......................................................... 800/3
See application file for complete search history.

(56) References Cited

U.S. PATENT DOCUMENTS

2002/0049986 A1*  4/2002  Farber et al. ............... 800/3
2004/0209279 A1  10/2004  Wu et al.
2007/0116645 A1*  5/2007  Farber et al. ............. 424/9.2

OTHER PUBLICATIONS

Babin et al 1997, Proc. Natl. Acad, Sci. USA 9:8622-8627.*
Marza et al 2005, Developmental Dynamics 232:506-518.*
Alimuddin et al., "Enhancement of EPA and DHA biosynthesis by over-expression of masu salmon Δ6-desaturase-like gene in zebrafish," Trangenic Research (2005) 14:159-165.
Dias et al., "Dietary protein source affects lipid metabolism in the European seabass (*Dicentrarchus labraz*)," Comparative Biochemistry and Physiology, Part A 142 (2005) 19-31.
Giffo-Schmidtt, Beate, International Preliminary Examination Report and Written Opinion, PCT/US2007/079927, International Bureau of WIPO, Apr. 15, 2009.
Hansson et al., "The immune response in atherosclerosis: a double-edged sword," Nat. Rev. Immunol., 508-519, Jul. 2006, vol. 6.
Hiriyanna, Kelaginamane, International Search Report, WO2008/048773A3, PCT/US07/79927, International Bureau of WIPO, Sep. 17, 2008.
Hiriyanna, Kelaginamane, Written Opinion, PCT/US07/79927, International Bureau of WIPO, Jun. 18, 2008.
Ho et al., "Lipid Metabolism in Zebrafish," Methods in Cell Biology, vol. 76, 2004, pp. 87-108.
Marza et al., "Developmental Expression and Nutritional Regulation of a Zebrafish Gene Homologous to Mammalian Microsomal Triglyceride Transfer Protein Large Subunit," Developmental Dynamics, 232:506-518, 2005.
Meir et al., "Atherosclerosis in the Apolipoprotein E-Deficient Mouse: A Decade of Progress," (2004) Atherioscler Thromb Vasc Biol. 24:1006-1014.
Schlegel et al., "Microsomal Triglyceride Transfer Protein Is Required for Yolk Lipid Utilization and Absorption of Dietary Lipids in Zebrafish Larvae," Biochemistry, 2006, 45, 15179-15187.
Zon et al., "In Vivo Drug Discovery in the Zebrafish," Jan. 2005, Nat. Review, vol. 4, pp. 35-44.

* cited by examiner

*Primary Examiner* — Scott Long
*Assistant Examiner* — Kelaginamane T Hiriyanna
(74) *Attorney, Agent, or Firm* — Gregory P. Einhorn; Greer Burns & Crain Ltd.

(57) ABSTRACT

The invention provides genetically altered fish of the family Cyprinidae, or genus *Danio*, including zebrafish (*Danio rerio*) and host cells from these animals, where the fish have been genetically altered to lack or have a modified gene related to lipid metabolism, for example, an ApoE, ApoAI and/or LDL-R gene. In another aspect, the invention is directed to drug design or discovery using the animal or cell models of the invention and/or wild type zebrafish, and by administering an altered diet and/or environment to the animal of invention. The invention also provides methods for screening for a compound capable of ameliorating or preventing or reversing: atherosclerosis; hyperlipidemia; lipoprotein oxidation; the accumulation of lipid in a blood vessel wall; vascular inflammation associated with lipid accumulation in a blood vessel wall; acute atherosclerosis-associated events; heart attack; stroke.

15 Claims, 12 Drawing Sheets lateral view lateral view virtual cross section virtual cross section

MODELS OF ATHEROSCLEROSIS, HYPERLIPIDEMIA, LIPOPROTEIN OXIDATION AND BLOOD VESSEL INFLAMMATION AND METHODS FOR MAKING AND USING THEM

TECHNICAL FIELD

This invention relates to molecular and cellular biology, biochemistry, molecular genetics, gene therapy, and drug design and discovery. In one aspect, the invention is directed to genetically altered fish of the family Cyprinidae, or genus *Danio*, including zebrafish (*Danio rerio*) and host cells and cell lines from these animals, where the fish have been genetically altered to lack or have a modified gene related to lipid metabolism, for example, an apolipoprotein E (ApoE), apolipoprotein A-I (ApoAI) and/or a low density lipoprotein receptor (LDL-R) gene. In another aspect, the invention is directed to drug design or discovery using the animal or cell models of the invention and/or wild type zebrafish, and by administering an altered diet and/or environment to the animal of invention.

BACKGROUND

Atherosclerosis is an inflammatory disease of blood vessels resulting in the growth of deposits of fatty substances, cholesterol, cellular waste products, calcium and other substances in the inner lining of an artery. This buildup is called plaque. It usually affects large and medium-sized arteries. Plaques can grow large enough to significantly reduce the blood flow through an artery. But most of the damage occurs when they become fragile and rupture. Plaques that rupture cause blood clots that can block blood flow or break off and travel to another part of the body. If either happens and blocks a blood vessel that feeds the heart, it causes a heart attack. If it blocks a blood vessel that feeds the brain, it causes a stroke.

Atherosclerosis starts when high content of cholesterol in the blood (hypercholesterolemia) leads to the lipid accumulation in the artery wall. This can start even in the fetus if the mother is hypercholesterolemic and progresses during the lifetime. Lipid accumulated in the artery wall undergoes oxidation and attracts inflammatory cells, monocytes, which differentiate into macrophages and take up the lipid. Resulting lipid-loaded macrophage "foam" cells residing in the artery inner layer (intima) are a hallmark of early atherosclerotic lesions. They further contribute to chronic vascular inflammation and the plaque growth. Therefore, studying the mechanisms of macrophage recruitment, lipid uptake and inflammation is important for understanding the pathogenesis of atherosclerosis. A feasible in vivo model of vascular lipid accumulation and inflammation will be also valuable for drug discovery.

Hyperlipidemia and hypercholesterolemia are developed as a consequence of an altered expression of genes regulating lipid metabolism and/or an altered dietary intake of lipids. In mammals, apolipoprotein E (ApoE), apolipoprotein A-I (ApoAI) and low density lipoprotein receptor (LDL-R) are critical proteins that regulate metabolism of lipoproteins, although many other genes are involved.

Current animal models of atherosclerosis: In an effort of establishing animal models of atherosclerosis researchers recreate in animals two major causative factors of the disease in humans, high cholesterol content in blood and high blood pressure. The latter is achieved by administration of high doses of angiotensin. However, the most popular models of atherosclerosis are the ones that achieve high levels of cholesterol in plasma. There are two animal species currently used to model atherosclerosis, hypercholesterolemic rabbits and genetically modified mice. Mouse models are especially widely utilized due to the availability of many transgenic and knockout strains.

Feeding atherosclerosis-susceptible mouse strains (C57BL6) high-fat, high-cholesterol diet causes the development of a very minimal atherosclerotic disease. However, this is greatly accelerated and increased in the mice deficient of either of two genes, which encode the proteins responsible for normal lipid delivery, the low-density lipoprotein receptor (LDLR) and apolipoprotein E (ApoE). The LDLR is on the surface of eventually every cell in the body; it recognizes LDL particles and, via the LDL uptake, the cells get nutrients, including fatty acids and cholesterol. ApoE is a part of lipoprotein particles and it also participates in the cellular uptake of lipid nutrients. The absence of either LDLR or ApoE, combined with the feeding a high-fat, high cholesterol diet, leads to the accumulation of high levels of LDL (the major carrier of cholesterol in blood) in plasma and eventually to its accumulation in artery wall and atherosclerosis.

Thus, $LDLR^{-/-}$ or $ApoE^{-/-}$ mice placed on high-fat diets are currently the two major animal models of atherosclerosis. Although having numerous advantages, these mouse models also have important limitations: A. Relatively long periods of pregnancy, maturation and cholesterol feeding, total from 6 to 12 months; B. A relatively high cost of maintaining of a mouse colony and numerous regulations for the handling of the mammals; C. A complex and labor intensive morphological analysis of atherosclerotic lesions; D. Atherosclerotic lesions in most cases can be analyzed only postmortem, e.g. at one time point only. Existing live animal imaging techniques are inadequate, of low resolution and often use radioactive materials.

SUMMARY

The invention provides stably genetically altered fish of the family Cyprinidae comprising at least one gene of lipid metabolism, such as genetically altered ApoE, ApoAI and/or LDL-R gene locus. The invention provides fish that have been genetically altered to lack or have a modified gene related to lipid metabolism; the genes can be e.g., an ApoE, ApoAI and/or LDL-R gene. In one aspect, the fish is of the family *Danio*, e.g., a zebrafish (*Danio rerio*). The invention provides isolated or cultured cells or tissues, or cell lines, derived from the fish of the invention. In one aspect, the gene or a set of genes related to lipid metabolism, e.g., the ApoE, ApoAI and/or LDL-R gene locus, are completely or partially knocked out in any combination; for example, in one aspect, only the ApoE, ApoAI and/or LDL-R are completely or partially knocked out, or alternatively some or all of these, or other lipid metabolism genes, are also completely or partially knocked out.

The invention provides stably genetically altered fish of the family Cyprinidae comprising or consisting of (a) an exogenous gene or a set of genes related to lipid metabolism, including the genes and/or polypeptides (or the sequence encoding them) illustrated or referenced in FIG. 6, FIG. 7, FIG. 8 and/or FIG. 9; (b) at least one gene from a genetically (sequence) altered ApoE, ApoAI and/or LDL-R gene locus; (c) a deleted, or "knocked out" homologous gene or a set of genes related to lipid metabolism; (d) the fish of (a) or (c), wherein the gene or a set of genes related to lipid metabolism comprise or consist of an ApoE, ApoAI and/or LDL-R gene; or (e) any combination of (a) to (d).

In one aspect, at least one nucleic acid residue of the gene or a set of genes related to lipid metabolism, e.g., ApoE, ApoAI and/or LDL-R gene locus, is altered or removed, or one or several heterologous sequences is/are inserted into the gene or a set of genes related to lipid metabolism, e.g., ApoE, ApoAI and/or LDL-R gene locus, or an endogenous sequence is rearranged in the gene or a set of genes related to lipid metabolism, e.g., ApoE, ApoAI and/or LDL-R gene locus. In one aspect, the gene or a set of genes related to lipid metabolism, e.g., ApoE, ApoAI and/or LDL-R gene locus is modified such that no or less amount of gene or a set of genes related to lipid metabolism, e.g., ApoE, ApoAI and/or LDL-R, message (transcript) and/or polypeptide is expressed. In one aspect, the gene or a set of genes related to lipid metabolism, e.g., ApoE, ApoAI and/or LDL-R gene locus, is modified such that the polypeptides, e.g., ApoE, ApoAI and/or LDL-R polypeptides, have no or less or altered activity.

The invention provides methods and/or models for studying the biology or pathology of lipoprotein metabolism and atherosclerosis or any inflammation associated with lipid accumulation, or for finding compounds capable of ameliorating or preventing or reversing: atherosclerosis; hyperlipidemia; lipoprotein oxidation; the accumulation of lipid in a blood vessel wall; vascular inflammation associated with lipid accumulation in a blood vessel wall; acute atherosclerosis-associated events; heart attack; stroke; or a combination thereof, comprising: maintaining a fish of the family Cyprinidae under conditions comprising an altered diet and/or environmental conditions conducive to initiating or maintaining accumulation of lipid in a blood vessel wall of the fish, or conditions conducive to initiating or maintaining atherosclerosis. In one aspect, the altered diet comprises a high fat diet (an enriched fat diet). In one aspect, the altered diet comprises a high cholesterol diet (an enriched cholesterol diet). In one aspect, the altered diet comprises a fluorescently labeled lipid. In one aspect, the fish is a wild type or a genetically altered fish of any one of the invention.

The invention provides methods for screening for a compound capable of ameliorating or preventing or reversing: atherosclerosis; hyperlipidemia; lipoprotein oxidation; the accumulation of lipid in a blood vessel wall; vascular inflammation associated with lipid accumulation in a blood vessel wall; acute atherosclerosis-associated events; heart attack; stroke, comprising: (a) providing a test compound; (b) administering the test compound to (i) a genetically altered fish of any one of the invention; (ii) a fish of the family Cyprinidae under conditions comprising an altered diet and/or environmental conditions conducive to initiating or maintaining hyperlipidemia, lipoprotein oxidation, accumulation of lipid in a blood vessel wall of the fish, or conditions conducive to initiating or maintaining atherosclerosis; or (iii) the genetically altered fish of (i) under the diet and/or environmental conditions of (ii); (c) determining if the test compound ameliorates, prevents and/or reverses atherosclerosis and/or the accumulation of lipid in a blood vessel wall and/or vascular inflammation associated with lipid accumulation in a blood vessel wall. In one aspect, the test compound is a small molecule, a polypeptide, a peptide, a nucleic acid, an siRNA, a polysaccharide or a lipid. In one aspect, the test compound is designed to target and/or increase or decrease the activity of: a matrix metalloproteinase, a lipoxygenase, a cyclooxygenase a phospholipase, a toll-like receptor, a NADPH oxidase, a nuclear receptor, a transcription factor NF-κB associated gene expression, macrophage lipid uptake, endothelial adhesion molecules and/or monocyte recruitment, smooth muscle cell growth and migration, apoptosis of vascular cells, phagocytosis of apoptotic cells, activation of T- and B-1 cells in the lesions, or a combination thereof.

Also provided herein are kits comprising cells of the invention including instructions for practicing the methods provided herein.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

FIG. 3 illustrates a confocal microscope image of disturbed endothelial cell morphology in the dorsal aorta of a zebrafish fed high-cholesterol diet, as described in detail, below.

DETAILED DESCRIPTION

The invention provides a novel fish (e.g., zebrafish) model to study mechanisms of and finding therapies against hyperlipidemia, lipoprotein oxidation, accumulation of lipid in the blood vessel wall and associated inflammation, including vascular inflammation. These processes can be rate-limiting steps in the formation of atherosclerotic lesions in humans and further promote the advanced lesion development, which may eventually result in heart attack or ischemic stroke, the two major causes of mortality in developed countries. Thus, the invention provides a model to study mechanisms of and finding therapies against (e.g., compositions and methods for the amelioration of) atherosclerotic lesions in humans, heart attack or ischemic stroke, hyperlipidemia, lipoprotein oxidation, accumulation of lipid in the blood vessel wall and associated inflammation, including vascular inflammation.

Figure 9:
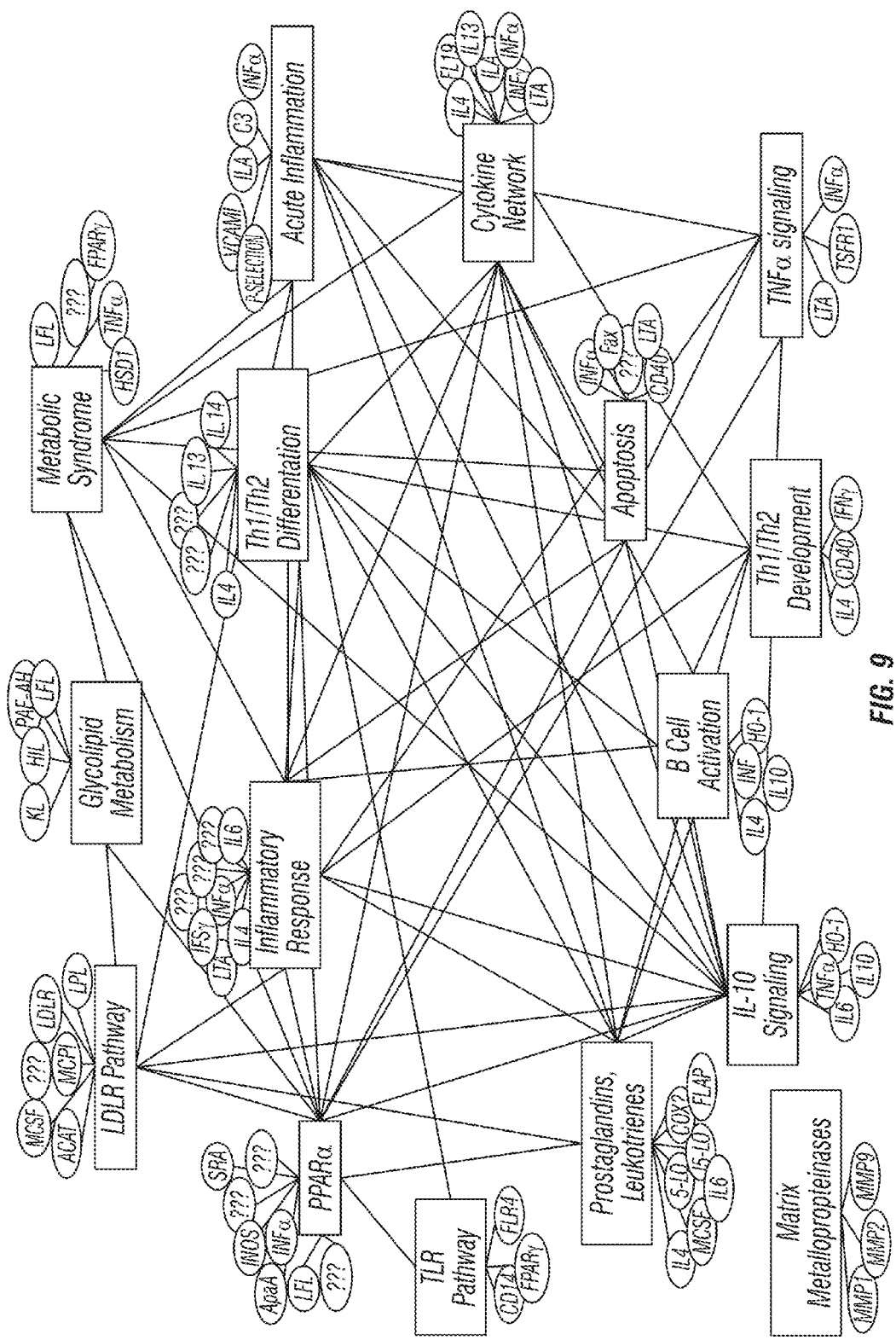
FIG. 9 illustrates an atherosclerosis pathway interaction network, and shows a schematic representation of interactions between 16 biological and metabolic pathways that contain genes associated with atherosclerosis, and one or several of these polypeptide and/or genes, including their fish homologues (counterparts), can be used to practice this invention.
Figure 10:
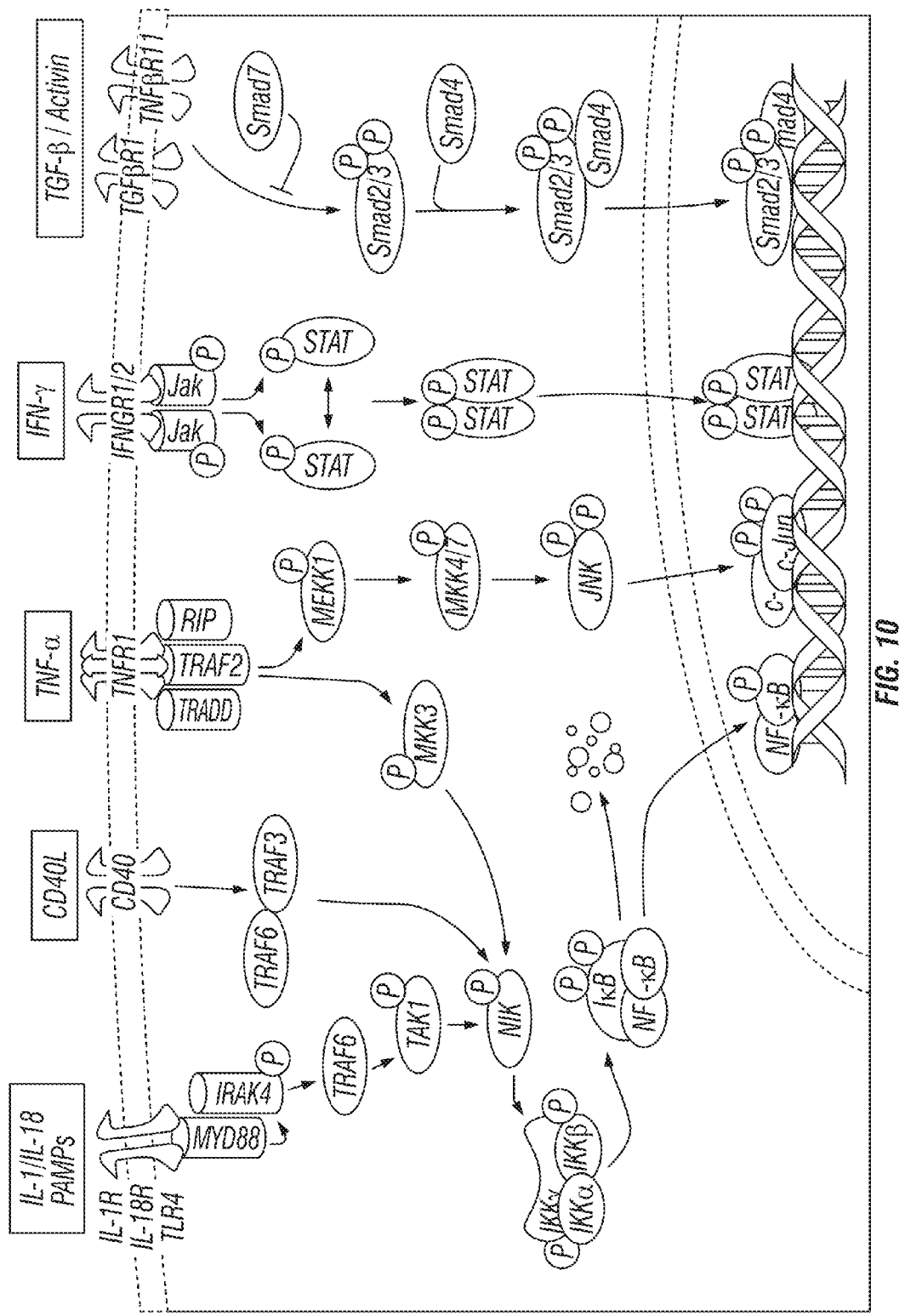
FIG. 10 illustrates signaling pathways involved in atherogenesis, and one or several of these polypeptide and/or genes, including their fish homologues (counterparts), can be used to practice this invention.
Figure 11:
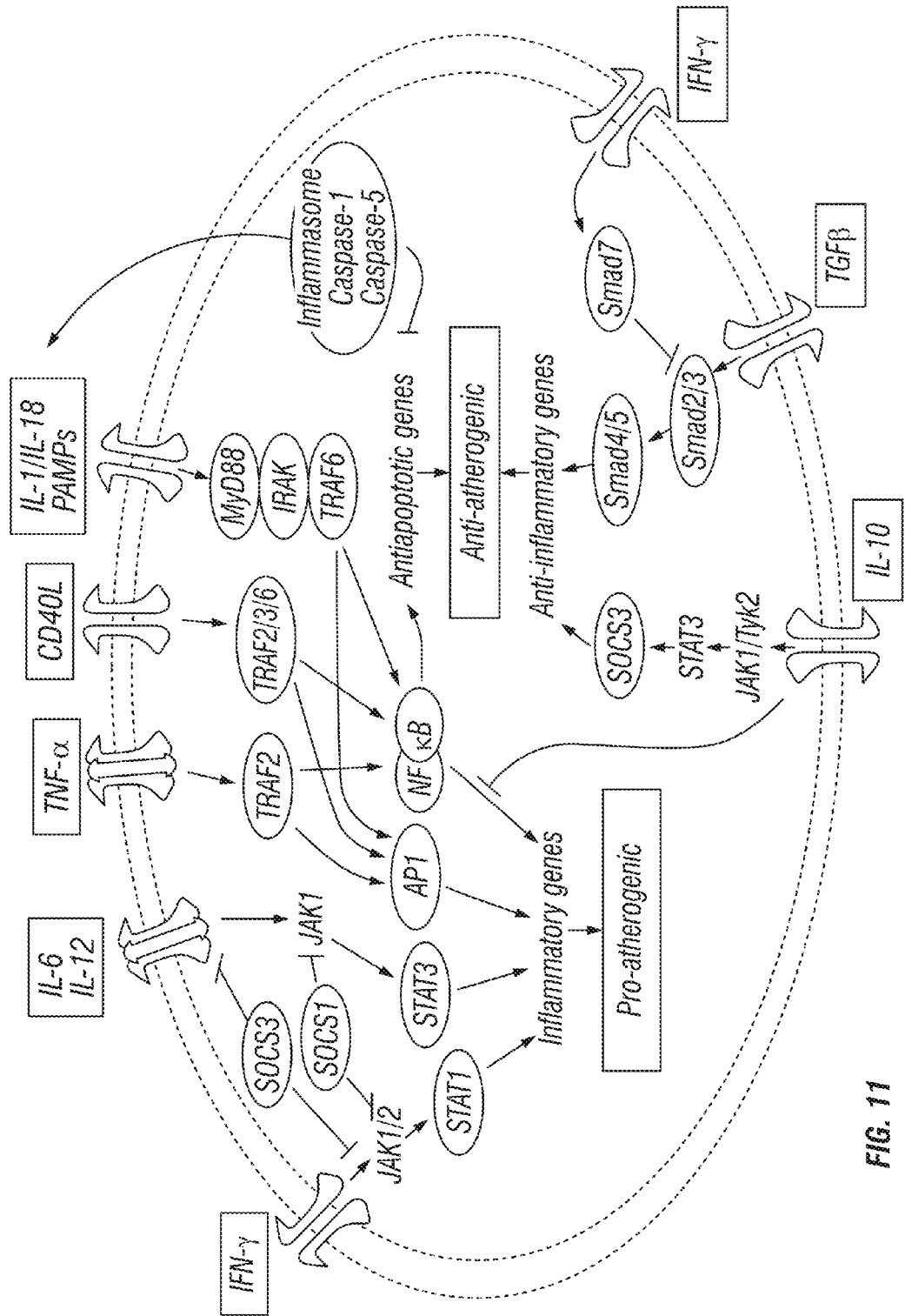
FIG. 11 illustrates genes and proteins, e.g., enzymes, involved in cross-talks between proinflammatory/proatherogenic and anti-inflammatory/antiatherogenic signal transduction pathways, and one or several of these polypeptide and/or genes, including their fish homologues (counterparts), can be used to practice this invention Like reference symbols in the various drawings indicate like elements.

In one aspect, the invention provides stable genetically altered fish of the family Cyprinidae comprising or consisting of (a) an exogenous gene or a set of genes related to lipid metabolism, e.g., as set forth in FIG. 6, FIG. 7, FIG. 8, FIG. 9, FIG. 10 and/or FIG. 11; (b) at least one gene from a genetically (sequence) altered ApoE, ApoAI and/or LDL-R gene locus; (c) a deleted, or "knocked out" homologous gene or a set of genes related to lipid metabolism; (d) the fish of (a) or (c), wherein the gene or a set of genes related to lipid metabolism comprise or consist of an ApoE, ApoAI and/or LDL-R gene; or (e) any combination of (a) to (d). FIG. 9 illustrates an atherosclerosis pathway interaction network, and shows a schematic representation of interactions between sixteen biological and metabolic pathways that contain genes associated with atherosclerosis, and one or several of these genes, including their fish homologues (counterparts), can be used to practice this invention. The connections between the pathways illustrate the presence of common atherosclerosis genes in two pathways. IL-10, interleukin-10; LDLR, LDL receptor; PPARα, peroxisome proliferator-activated receptor α; Th1/Th2, T helper cell 1/2; TLR, toll-like receptor; TNF-α, tumor necrosis factor-α; genes encoding these proteins, including their fish homologues (counterparts), also can be used to practice this invention.

FIG. 10 illustrates signaling pathways involved in atherogenesis, and one or several of these polypeptide and/or genes, including their fish homologues (counterparts), can be used to practice this invention; for example, genes encoding the following can be manipulated in the genetically altered fish of this invention: proinflammatory cytokines (IL-1, IL-18) and pathogens (represented as pathogen-associated molecular patterns, PAMP), as well as nonpathogen activators of TLR, act through distinct signaling pathways that converge on the activation of NF-κB; MyD88 functions as an adaptor between receptors of the TLR or IL-1R families and downstream signaling kinases; following association of MyD88 with IL-1-associated kinase IRAK-4, IRAK-4 is autophosphorylated, dissociates from the receptor complex, and interacts with TNF-receptor-associated factor-6 (TRAF-6), which also mediates CD40 signaling; once activated, TRAF6 associates with the MAP3 kinase TAK1 (716); from TAK1, two signaling pathways diverge; one ultimately leads to NF-κB activation and the other to MAP kinase activation; in its inactive form, NF-κB is bound to inhibitor of κB (IK-κBα/β) in the cytoplasm and consists of an LB kinase (IKK) complex containing two kinases IKKα and IKKβ, and the regulatory protein IKKγ (also named NEMO); IKK activation initiates IκBα/β phosphorylation; phosphorylated LB is then ubiquitinated, leading to its degradation by the 26S proteasome; this releases NF-κB dimers from the cytoplasmic NF-κB-IκB complex, allowing them to translocate to the nucleus. JNK phosphorylation is mediated by two MAPK kinases (MAPKKs), MKK4 and MKK7, that they can cooperatively activate JNK. Both kinases are required for full activation of JNK by environmental stressors, and MKK7 is essential for JNK activation by TNR engagement. Tyrosine phosphorylation activates the cytosolic inactive STATs, resulting in their nuclear translocation and gene activation. This pathway was originally found to be activated by IFNs, but a number of cytokines, growth factors, and hormonal factors also activate JAK and/or STAT proteins. IFN-γ utilizes JAK1 and JAK2, and usually activates STAT1. TGF-β-triggered signals are transduced by proteins belonging to the Smad (for vertebrate homologs of Sma and Mad) family. The type I receptor recognizes and phosphorylates Smad2 and Smad3, which associates with Smad4, forming complexes that participate in DNA binding and recruitment of transcription factors. Smad3 may also have antagonistic properties, as it plays a critical role in TGF-β-dependent repression of vascular inflammation by inhibiting AP-1 activity. Smad7 inhibits Smad2 and Smad3 phosphorylation. See, e.g., Tedgui et al., Physiol. Rev. 86: 515-581, 2006.

FIG. 11 illustrates genes and proteins, e.g., enzymes, involved in cross-talks between proinflammatory/pro-atherogenic and anti-inflammatory/antiatherogenic signal transduction pathways, and one or several of these polypeptide and/or genes, including their fish homologues (counterparts), can be used to practice this invention; for example, genes encoding the following can be manipulated in the genetically altered fish of this invention: inhibitory Smads such as Smad7 downstream of IFN-γ signaling associate with activated receptors and interfere with Smad2 and Smad3 binding; IFN-γ, the anti-inflammatory cytokine IL-10 also activates JAK and/or STAT proteins; IL-10/IL-10R interaction activates JAK1 and Tyk2, leading to STAT3 and SOCS3 activation, which is central for the anti-inflammatory responses of IL-10 in macrophages; an inflammasome may be a central link between apoptosis and inflammation in pathological conditions; NF-κB may have a dual role in atherosclerosis, being pro-atherogenic through its proinflammatory properties, and antiatherogenic through its anti-apoptotic activities. See, e.g., Tedgui et al., Physiol. Rev. 86: 515-581, 2006.

In one aspect, a zebrafish model of atherosclerosis is generated by altering dietary and environmental conditions and/or a genetic background of zebrafish. Examples of such alterations are high cholesterol diet and ApoE knockdown:

1. Feeding zebrafish with a diet enriched with cholesterol leads to lipid accumulation in blood vessels and atherosclerosis. Addition of a fluorescently labeled lipid facilitates visualizing the lipid accumulation in blood vessels.

2. Knockdown of ApoE, combined with high-cholesterol diet, accelerates and/or increases atherosclerosis burden in zebrafish.

3. Development of vascular inflammation and atherosclerosis is observed in an optically transparent zebrafish with fluorescent vasculature (fli:EGFP) and in real time using a fluorescent microscope.

In one aspect, the methods of the invention are practiced using optical transparence. Optical transparence of zebrafish makes it a unique model for a real-time, multiparametic in vivo study of the processes involved in atherosclerosis. In addition, the models of this invention make screening of drug candidates for atherosclerosis therapy feasible and cost effective.

The fish and cells of the invention, e.g., zebrafish, provide models for various developmental, physiological and pathological processes. The use of fish and cells of the invention are optimal for the development of a model of atherosclerosis for the following reasons:

A. A zebrafish embryo/larva is optically transparent for up to 30 days, which allows conducting real time microscopic observations in a live animal. Zebrafish can be easily genetically modified. For example, in a transgenic zebrafish strain with enhanced green fluorescence protein (EGFP) constitutively expressed in endothelial cells (the cells that cover the inner surface of blood vessels), fli:EGFP, vascular system is readily visualized under a fluorescent microscope.

B. A zebrafish colony maintenance is by far more economic than the maintenance of a mouse colony.

C. New drug candidates can be easily tested in a zebrafish model by simply adding them to the water in a fish tank. This makes zebrafish an ultimate in vivo model for new drug development.

D. Zebrafish embryo feeds from yolk for the first 5 days post fertilization and is free feeding thereafter. The yolk sac constantly forms lipoproteins, which then gain entry into circulation and supply nutrients to the tissues. Remarkably, zebrafish ApoE, which is homologous to human and mouse ApoE, is highly expressed in the yolk sac. This suggests that the mechanisms of lipoprotein delivery are similar in zebrafish and in mammals, and regulated manipulation with these processes gains a suitable model for atherosclerosis, a disease originating from disturbed lipid metabolism.

Thus, this invention provides applications of finding therapeutic targets and pre-clinical testing of the therapies to prevent and/or slow down the development of atherosclerosis. The potential targets may include but not limited to:
  macrophage matrix metalloproteinases,
  12/15-lipoxygenase,
  5-lipoxygenase,
  toll-like receptors 2 and 4,
  NF-kappaB associated gene expression,
  macrophage lipid uptake,
  endothelial adhesion molecules and monocyte recruitment,
  smooth muscle cell growth and migration,
  apoptosis of vascular cells,
  phagocytosis of apoptotic cells,
  activation of T- and B-1 cells in the lesions, and many others.

Feasibility and low cost of the zebrafish model, together with its access to real-time imaging of atherosclerotic processes in a live animal, make it an attractive object for commercial applications.

In another aspect of the invention, a nucleic acid used to practice the invention, including any gene or genes related to lipid metabolism e.g., a ApoE, ApoAI and/or LDL-R gene locus, an expression vector used to insert or express any gene or genes related to lipid metabolism, such as a ApoE, ApoAI and/or LDL-R gene locus, in a cell, cell line, or a fish of the invention, or any target sequence, can comprise a reporter or a marker gene (including nucleic acid sequences that encode proteins that can be used for reporting activity, e.g., enzymes or epitopes). In one aspect, the reporter or marker gene is used to monitor gene (e.g., an ApoE, ApoAI and/or LDL-R gene locus) expression, e.g., one, several or all coding sequence in the locus can be marked with the same or different markers. In one aspect, the reporter or marker gene is used to monitor gene suppression or silencing. In one aspect of the invention, the reporter gene comprises green fluorescent protein. Any compound, fluorophore, label, isotope, protein or gene that has a reporting or marking function can be used in the methods provided herein.

In another aspect of the invention, nucleic acids used to practice the invention, including any gene or genes related to lipid metabolism, e.g., ApoE, ApoAI and/or LDL-R gene locus, an expression vector, or any target sequences are inserted into the genome of a host cell by e.g. a vector, a virus or any nucleic acid shuttling or insertional mechanism. For example, a nucleic acid sequence can be inserted into a genome or a vector by a variety of procedures. In one aspect, the sequence is ligated to the desired position in the vector following digestion of the insert and the vector with appropriate restriction endonucleases. Alternatively, blunt ends in both the insert and the vector may be ligated. In one aspect, viral long terminal repeats (LTRs) are inserted in a flanking pattern to effect insertion of a desired sequence (e.g., ApoE, ApoAI and/or LDL-R and/or another gene locus) into a genome. In one aspect, sequences homologous to a genome target sequence (targeting where in the genome it is desired to insert a desired nucleic acid, e.g., ApoE, ApoAI and/or LDL-R and/or another gene locus) are inserted in a flanking pattern to effect insertion of the desired sequence into a genome. A variety of cloning techniques are known in the art, e.g., as described in Ausubel and Sambrook. Such procedures and others are deemed to be within the scope of those skilled in the art.

The vector used to make or practice the invention can be chosen from any number of suitable vectors known to those skilled in the art, including cosmids, YACs (Yeast Artificial Chromosomes), megaYACS, BACs (Bacterial Artificial Chromosomes), PACs (P1 Artificial Chromosome), MACs (Mammalian Artificial Chromosomes), a whole chromosome, or a small whole genome. The vector also can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook. Particular bacterial vectors which can be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, DR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell. In one aspect of the invention, target sequences are integrated into genomes using a lentiviral feline immunodeficiency (FIV) vector for the transduction process.

The invention provides a fish comprising deleted or modified gene or genes related to lipid metabolism, e.g., ApoE, ApoAI and/or LDL-R) gene loci. In some aspects, the (fish) endogenous gene or genes related to lipid metabolism, e.g., ApoE, ApoAI and/or LDL-R gene locus, has been completely, or partially, disabled ("knocked out"). Nucleic acids used to practice the invention, including any gene or genes related to lipid metabolism, e.g., the fish ApoE, ApoAI and/or LDL-R gene locus, and vectors comprising this or other nucleic acids (e.g., including other ApoE, ApoAI and/or LDL-R gene loci segments for making "knockout" animals) can be made, isolated and/or manipulated by, e.g., cloning and expression of cDNA libraries, amplification of message or genomic DNA by PCR, and the like. In practicing the methods of the invention, homologous or exogenous genes (e.g., gene or genes related to lipid metabolism, e.g., such as ApoE, ApoAI and/or LDL-R loci genes) can be modified by manipulating a template nucleic acid, as described herein. The invention can be practiced in conjunction with any method or protocol or device known in the art, which are well described in the scientific and patent literature.

A fish of the invention include both animals having stably inserted exogenous or homologous gene or genes related to lipid metabolism, e.g., ApoE, ApoAI and/or LDL-R sequences (e.g., a complete or partial ApoE, ApoAI and/or LDL-R gene locus), unstable genomic inserts, mitochondrial inserts, or episomal inserts, e.g., as artificial chromosomes that are episomal to the endogenous chromosomes of the animal.

The nucleic acids used to practice this invention, whether RNA, iRNA, siRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066. Alternatively, nucleic acids can be obtained from commercial sources.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., *Molecular Cloning: A Laboratory Manual* (2nd ed.), Vols. 1-3, Cold Spring Harbor Laboratory, (1989); *Current Protocols in Molecular Biology*, Ausubel, ed. John Wiley & Sons, Inc., New York (1997); *Laboratory Techniques in Biochemistry and Molecular Biology: Hybridization with Nucleic Acid Probes*, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In practicing the invention, nucleic acids of the invention or modified nucleic acids of the invention, can be reproduced by amplification. Amplification can also be used to clone or modify the nucleic acids of the invention. Thus, the invention provides amplification primer sequence pairs for amplifying nucleic acids of the invention. One of skill in the art can design amplification primer sequence pairs for any part of or the full length of these sequences.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library are amplified.

The skilled artisan can select and design suitable oligonucleotide amplification primers. Amplification methods are also well known in the art, and include, e.g., polymerase chain reaction, PCR (see, e.g., *PCR Protocols, A Guide to Methods and Applications*, ed. Innis, Academic Press, N.Y. (1990) and *PCR Strategies* (1995), ed. Innis, Academic Press, Inc., N.Y., ligase chain reaction (LCR) (see, e.g., Wu (1989) *Genomics* 4:560; Landegren (1988) *Science* 241:1077; Barringer (1990) *Gene* 89:117); transcription amplification (see, e.g., Kwoh (1989) Proc. Natl. Acad. Sci. USA 86:1173); and, self-sustained sequence replication (see, e.g., Guatelli (1990) *Proc. Natl. Acad. Sci. USA* 87:1874); Q Beta replicase amplification (see, e.g., Smith (1997) *J. Clin. Microbiol.* 35:1477-1491), automated Q-beta replicase amplification assay (see, e.g., Burg (1996) *Mol. Cell. Probes* 10:257-271) and other RNA polymerase mediated techniques (e.g., NASBA, Cangene, Mississauga, Ontario); see also Berger (1987) *Methods Enzymol.* 152:307-316; Sambrook; Ausubel; U.S. Pat. Nos. 4,683,195 and 4,683,202; and Sooknanan (1995) *Biotechnology* 13:563-564.

The sequences of the nucleic acids, e.g., the genes or messages (mRNA), related to lipid metabolism, for example, an ApoE, ApoAI and/or LDL-R gene or message, used to practice this invention are well known in the art; for example:

In one aspect, human (*Homo sapiens*) apolipoprotein E (ApoE) sequences can be used (either from complete or partial genomic (gene) or mRNA, or message, sequence) to practice this invention, e.g., in one aspect, human ApoE sequence is inserted into an animal model or cell or cell line of this invention as an exogenous sequences; e.g., in one aspect, all or part of the message for human ApoE is used:

(SEQ ID NO: 1)

```
  1 gggatccttg agtcctactc agccccagcg gaggtgaagg acgtccttcc ccaggagccg 61 actggccaat cacaggcagg aagatgaagg ttctgtgggc tgcgttgctg gtcacattcc 121 tggcaggatg ccaggccaag gtggagcaag cggtggagac agagccgag cccgagctgc 181 gccagcagac cgagtggcag agcggccagc gctgggaact ggcactgggt cgcttttggg 241 attacctgcg ctgggtgcag acactgtctg agcaggtgca ggaggagctg ctcagctccc 301 aggtcaccca ggaactgagg gcgctgatgg acgagaccat gaaggagttg aaggcctaca
```

```
361 aatcggaact ggaggaacaa ctgacccgg tggcggagga dacgcgggca cggctgtcca 421 aggagctgca ggcggcgcag gcccggctgg gcgcggacat ggaggacgtg tgcggccgcc 481 tggtgcagta ccgcggcgag gtgcaggcca tgctcggcca gagcaccgag gagctgcggg 541 tgcgcctcgc ctcccacctg cgcaagctgc gtaagcggct cctccgcgat gccgatgacc 601 tgcagaagcg cctggcagtg taccaggccg gggcccgcga gggcgccgag cgcggcctca 661 gcgccatccg cgagcgcctg gggccctgg tggaacaggg ccgcgtgcgg gccgccactg 721 tgggctccct ggccggccag ccgctacagg agcgggccca ggcctggggc gagcggctgc 781 gcgcgcggat ggaggagatg ggcagccgga cccgcgaccg cctggacgag gtgaaggagc 841 aggtggcgga ggtgcgcgcc aagctggagg agcaggccca gcagatacgc ctgcaggccg 901 aggccttcca ggcccgcctc aagagctggt tcgagcccct ggtggaagac atgcagcgcc 961 agtgggccgg gctggtggag aaggtgcagg ctgccgtggg caccagcgcc gccctgtgc 1021 ccagcgacaa tcactgaacg ccgaagcctg cagccatgcg accccacgcc acccgtgcc 1081 tcctgcctcc gcgcagcctg cagcgggaga ccctgtcccc gccccagccg tcctcctggg 1141 gtggaccta gtttaataaa gattcaccaa gtttcacgca aaaaaaaaa aaaaaaaaa 1201 aaaaaaaaaa aaaaaaaaa aaa
```

Alternatively, all or part of a sequence encoding human ApoE is used, e.g., the human ApoE amino acid sequence can be:

(SEQ ID NO: 2)
MKVLWAALLVTFLAGCQAKVEQAVETEPEPELRQQTEWQSGQRWELALGR
FWDYLRWVQTLSEQVQEELLSSQVTQELRALMDETMKELKAYKSELEEQL
TPVAEETRARLSKELQAAQARLGADMEDVCGRLVQYRGEVQAMLGQSTEE
LRVRLASHLRKLRKRLLRDADDLQKRLAVYQAGAREGAERGLSAIRERLG
PLVEQGRVRAATVGSLAGQPLQERAQAWGERLRARMEEMGSRTRDRLDEV
KEQVAEVRAKLEEQAQQIRLQAEAFQARLKSWFEPLVEDMQRQWAGLVEK
VQAAVGTSAAPVPSDNH

In one alternative aspect, *Danio rerio* (zebrafish) apolipoprotein E (ApoE) sequences are used (either from complete or partial genomic (gene) or mRNA, or message, sequence) to practice this invention, e.g., in one aspect, zebrafish ApoE sequence is modified, knocked out, or modified and re-inserted into an animal model or cell or cell line of this invention as an altered (modified, mutated) endogenous sequence (including deletions, additions, base substitutions), or as an exogenous sequence; e.g., in one aspect, all or part of the message for zebrafish ApoE is used:

```
                                          (SEQ ID NO: 3)
  1 atcaacatga ggtctcttgt ggtattcttt gccctggcag ttttaactgg ctgccaggct 61 cgtagcctgt tccaggctga tgcccctcag cccagatggg aggagatggt ggaccgtttc 121 tggcagtatg tgtctgaact caacacacaa actgacggca tggtgcaaaa catcaagggc 181 tcccagctca gcagagagct tgacacacta attactgaca ccatggctga actgagctca 241 tacagtgaaa atctccaaac ccagatgacc ccatatgcct ctgatgctgc tggtcagctc 301 agtaaagatc ttcagctcct ggctggaaaa ctccaaactg acatgaccga cgctaaggaa 361 cgcagcactc agtacctgca agagctgaag accatgatgg agcaaaatgc agatgacgtg 421 aagaaccgtg tcggcaccta cacacgcaaa ctgaagaaac gcctgaacaa ggacacagag 481 gagatccgca acaccgtagc aacctacatg agtgagatgc agtcccgcgc ttcccaaaat 541 gctgatgcag tgaaggaccg tttccagcca tacatgagcc aggcccagga tggcgccacc
```

```
601 cagaaactgg gcgccattag cgagctgatg aaggcccagg cgcaggaggt gagcgagcag 661 ttggaggtcc aggctggagc tctgaaggag aagctggagg agacagccga gaacctacgc 721 acctctctgg agggccgtgt ggatgagctg accagcctcc tcgccccta ctcccagaag 781 atccgcgagc agctgcagga agtcatggac aagatcaagg aggccacagc agctcttccc 841 actcaggctt aagagctcca cacttaccta gtgttaacac caaacagaaa gaagaaggga 901 ggctttgtgt tactgaaatg tgcttttttc attctgtgag aggttgataa agtggttaac 961 aactggactc aattggacta gcactgtcct ttactggaca aaagaaatgc catgttactc 1021 accacgttta ctttctcagt attaacccat gtctgaggat atatttctgt tagcgtacag 1081 tagagcgaat ttaagatcaa tcaacttgtc tgtcttggag gctattttt ctagttagtg 1141 gggccaaact tggcgtcatt caaaataaat agtaatcaaa aggtgccttc agctgctgaa 1201 atgaatcaga acacatgaaa gatgagcttt gttagtcaac agtccacata taaatgcttg 1261 tttactttac atgtttgtgc actgatgtgt ttgaatttgt ttgcaataaa tgtgcgttct 1321 actacacaaa aaaaaaaaaa aaaaa
```

In one aspect, all or part of a sequence encoding zebrafish ApoE is used, e.g., the zebrafish ApoE amino acid sequence can be:

(SEQ ID NO: 4)
MRSLVVFFALAVLTGCQARSLFQADAPQPRWEEMVDRFWQYVSELNTQTD
GMVQNIKGSQLSRELDTLITDTMAELSSYSENLQTQMTPYASDAAGQLSK
DLQLLAGKLQTDMTDAKERSTQYLQELKTMMEQNADDVKNRVGTYTRKLK
KRLNKDTEEIRNTVATYMSEMQSRASQNADAVKDRFQPYMSQAQDGATQK
LGAISELMKAQAQEVSEQLEVQAGALKEKLEETAENLRTSLEGRVDELTS
LLAPYSQKIREQLQEVMDKIKEATAALPTQA

In one aspect, human (*Homo sapiens*) apolipoprotein A-I (ApoAI) sequences can be used (either from complete or partial genomic (gene) or mRNA, or message, sequence) to practice this invention, e.g., in one aspect, human ApoAI sequence is inserted into an animal model or cell or cell line of this invention as an exogenous sequences; e.g., in one aspect, all or part of the message for human ApoAI is used:

```
(SEQ ID NO: 5)
1 agagactgcg agaaggaggt cccccacggc ccttcaggat gaaagctgcg gtgctgacct 61 tggccgtgct cttcctgacg gggagccagg ctcggcattt ctggcagcaa gatgaacccc 121 cccagagccc ctgggatcga gtgaaggacc tggccactgt gtacgtggat gtgctcaaag 181 acagcggcag agactatgtg tcccagtttg aaggctccgc cttgggaaaa cagctaaacc 241 taaagctcct tgacaactgg gacagcgtga cctccacctt cagcaagctg cgcgaacagc 301 tcggccctgt gacccaggag ttctgggata acctggaaaa ggagacagag ggcctgaggc 361 aggagatgag caaggatctg gaggaggtga aggccaaggt gcagccctac ctggacgact 421 tccagaagaa gtggcaggag gagatggagc tctaccgcca gaaggtggag ccgctgcgcg 481 cagagctcca gagggcgcg cgccagaagc tgcacgagct gcaagagaag ctgagcccac 541 tgggcgagga gatgcgcgac cgcgcgcgcg cccatgtgga cgcgctgcgc acgcatctgg 601 ccccctacag cgacgagctg cgccagcgct tggccgcgcg ccttgaggct ctcaaggaga 661 acggcggcgc cagactggcc gagtaccacg ccaaggccac cgagcatctg agcacgctca 721 gcgagaaggc caagcccgcg ctcgaggacc tccgccaagg cctgctgccc gtgctggaga 781 gcttcaaggt cagcttcctg agcgctctcg aggagtacac taagaagctc aacacccagt 841 gaggcgcccg ccgccgcccc ccttcccggt gctcagaata aacgtttcca aagtggg
```

In one aspect, all or part of a sequence encoding human ApoAI is used, e.g., the human ApoAI amino acid sequence can be:

(SEQ ID NO: 6)
MKAAVLTLAVLFLTGSQARHFWQQDEPPQSPWDRVKDLATVYVDVLKDSG
RDYVSQFEGSALGKQLNLKLLDNWDSVTSTFSKLREQLGPVTQEFWDNLE
KETEGLRQEMSKDLEEVKAKVQPYLDDFQKKWQEEMELYRQKVEPLRAEL
QEGARQKLHELQEKLSPLGEEMRDRARAHVDALRTHLAPYSDELRQRLAA
RLEALKENGGARLAEYHAKATEHLSTLSEKAKPALEDLRQGLLPVLESFK
VSFLSALEEYTKKLNTQ

In one aspect, human (*Homo sapiens*) LDL-R sequences can be used (either from complete or partial genomic (gene) or mRNA, or message, sequence) to practice this invention, e.g., in one aspect, human LDL-R sequence is inserted into an animal model or cell or cell line of this invention as an exogenous sequences; e.g., in one aspect, all or part of the message for human LDL-R is used:

(SEQ ID NO: 7)
```
   1 cagaggctgc gagcatgggg ccctggggct ggaaattgcg ctggaccgtc gccttgctcc
  61 tcgccgcggc ggggactgca gtgggcgaca gatgcgaaag aaacgagttc cagtgccaag
 121 acgggaaatg catctcctac aagtgggtct gcgatggcag cgctgagtgc caggatggct
 181 ctgatgagtc ccaggagacg tgcttgtctg tcacctgcaa atccggggac ttcagctgtg
 241 ggggccgtgt caaccgctgc attcctcagt tctggaggtg cgatggccaa gtggactgcg
 301 acaacggctc agacgagcaa ggctgtcccc caagacgtg ctcccaggac gagtttcgct
 361 gccacgatgg gaagtgcatc tctcggcagt tcgtctgtga ctcagaccgg gactgcttgg
 421 acggctcaga cgaggcctcc tgccggtgc tcacctgtgg tcccgccagc ttccagtgca
 481 acagctccac ctgcatcccc cagctgtggg cctgcgacaa cgaccccgac tgcgaagatg
 541 gctcggatga gtggccgcag cgctgtaggg gtctttacgt gttccaaggg gacagtagcc
 601 cctgctcggc cttcgagttc cactgcctaa gtggcgagtg catccactcc agctggcgct
 661 gtgatggtgg ccccgactgc aaggacaaat ctgacgagga aaactgcgct gtggccacct
 721 gtcgccctga cgaattccag tgctctgatg gaaactgcat ccatggcagc cggcagtgtg
 781 accgggaata tgactgcaag gacatgagcg atgaagttgg ctgcgttaat gtgacactct
 841 gcgagggacc caacaagttc aagtgtcaca gcggcgaatg catcaccctg acaaagtct
 901 gcaacatggc tagagactgc cgggactggt cagatgaacc catcaaagag tgcgggacca
 961 acgaatgctt ggacaacaac ggcggctgtt cccacgtctg caatgacctt aagatcggct
1021 acgagtgcct gtgccccgac ggcttccagc tggtggccca gcgaagatgc gaagatatcg
1081 atgagtgtca ggatcccgac acctgcagcc agctctgcgt gaacctggag ggtggctaca
1141 agtgccagtg tgaggaaggc ttccagctgg accccacac gaaggcctgc aaggctgtgg
1201 gctccatcgc ctacctcttc ttcaccaacc ggcacgaggt caggaagatg acgctggacc
1261 ggagcgagta caccagcctc atccccaacc tgaggaacgt ggtcgctctg gacacggagg
1321 tggccagcaa tagaatctac tggtctgacc tgtcccagag aatgatctgc agcacccagc
1381 ttgacagagc ccacggcgtc tcttcctatg acaccgtcat cagcagggac atccaggccc
1441 ccgacgggct ggctgtggac tggatccaca gcaacatcta ctggaccgac tctgtcctgg
1501 gcactgtctc tgttgcggat accaagggcg tgaagaggaa aacgttattc agggagaacg
1561 gctccaagcc aagggccatc gtggtggatc ctgttcatgg cttcatgtac tggactgact
1621 ggggaactcc cgccaagatc aagaaagggg gcctgaatgg tgtggacatc tactcgctgg
1681 tgactgaaaa cattcagtgg cccaatggca tcaccctaga tctcctcagt ggccgcctct
1741 actggttga ctccaaactt cactccatct caagcatcga tgtcaacggg gcaaccgga
1801 agaccatctt ggaggatgaa aagaggctgg cccaccccct tctccttggcc gtctttgagg
1861 acaaagtatt ttggacagat atcatcaacg aagccatttt cagtgccaac cgcctcacag
```

```
-continued
1921 gttccgatgt caacttgttg gctgaaaacc tactgtcccc agaggatatg gttctcttcc 1981 acaacctcac ccagccaaga ggagtgaact ggtgtgagag gaccaccctg agcaatggcg 2041 gctgccagta tctgtgcctc cctgccccgc agatcaaccc ccactcgccc aagtttacct 2101 gcgcctgccc ggacggcatg ctgctggcca gggacatgag gagctgcctc acagaggctg 2161 aggctgcagt ggccacccag gagacatcca ccgtcaggct aaaggtcagc tccacagccg 2221 taaggacaca gcacacaacc acccggcctg ttcccgacac ctcccggctg cctggggcca 2281 cccctgggct caccacggtg gagatagtga caatgtctca ccaagctctg ggcgacgttg 2341 ctggcagagg aaatgagaag aagcccagta gcgtgagggc tctgtccatt gtcctcccca 2401 tcgtgctcct cgtcttcctt tgcctggggg tcttccttct atggaagaac tggcggctta 2461 agaacatcaa cagcatcaac tttgacaacc ccgtctatca gaagaccaca gaggatgagg 2521 tccacatttg ccacaaccag gacggctaca gctacccctc gagacagatg gtcagtctgg 2581 aggatgacgt ggcgtgaaca
```

In one aspect, all or part of a sequence encoding human LDL-R is used, e.g., the human LDL-R amino acid sequence can be:

(SEQ ID NO: 8)
MGPWGWKLRWTVALLLAAAGTAVGDRCERNEFQCQDGKCISYKWVC

DGSAECQDGSDESQETCLSVTCKSGDFSCGGRVNRCIPQFWRCDGQVDCD

NGSDEQGCPPKTCSQDEFRCHDGKCISRQFVCDSDRDCLDGSDEASCPVL

TCGPASFQCNSSTCIPQLWACDNDPDCEDGSDEWPQRCRGLYVFQGDSSP

CSAFEFHCLSGECIHSSWRCDGGPDCKDKSDEENCAVATCRPDEFQCSDG

NCIHGSRQCDREYDCKDMSDEVGCVNVTLCEGPNKFKCHSGECITLDKVC

NMARDCRDWSDEPIKECGTNECLDNNGGCSHVCNDLKIGYECLCPDGFQL

VAQRRCEDIDECQDPDTCSQLCVNLEGGYKCQCEEGFQLDPHTKACKAVG

SIAYLFFTNRHEVRKMTLDRSEYTSLIPNLRNVVALDTEVASNRIYWSDL

SQRMICSTQLDRAHGVSSYDTVISRDIQAPDGLAVDWIHSNIYWTDSVLG

TVSVADTKGVKRKTLFRENGSKPRAIVVDPVHGFMYWTDWGTPAKIKKGG

LNGVDIYSLVTENIQWPNGITLDLLSGRLYWVDSKLHSISSIDVNGGNRK

TILEDEKRLAHPFSLAVFEDKVFWTDIINEAIFSANRLTGSDVNLLAENL

LSPEDMVLFHNLTQPRGVNWCERTTLSNGGCQYLCLPAPQINPHSPKFTC

ACPDGMLLARDMRSCLTEAEAAVATQETSTVRLKVSSTAVRTQHTTTRPV

PDTSRLPGATPGLTTVEIVTMSHQALGDVAGRGNEKKPSSVRALSIVLPI

VLLVFLCLGVFLLWKNWRLKNINSINFDNPVYQKTTEDEVHICHNQDGYS

YPSRQMVSLEDDVA

Other sequences used to practice this invention, including gene or genes corresponding to genes known to affect or be involved in lipid metabolism, including ApoE, ApoAI and/or LDL-R, from other species, including gene or genes affecting or involved in lipid metabolism in fish, e.g., fish from the family Cyprinidae, or genus *Danio*, including zebrafish (*Danio rerio*), can be routinely identified based on structural homology (e.g., sequence identify) and functional similarity with known genes, messages, proteins and sequences.

Cells and Tissues

The invention also provides cells and tissues (e.g., harvested from a fish of the invention) comprising altered, and/or a complete or partial gene or genes related to lipid metabolism, e.g., ApoE, ApoAI and/or LDL-R, gene loci. In one aspect of the invention, cells have gene expression that has been silenced by mutation, sequence deletion, or by transcriptional silencing, e.g., where the endogenous gene or genes related to lipid metabolism, e.g., ApoE, ApoAI and/or LDL-R loci genes, are completely or partially silenced by mutation, sequence deletion and/or by transcriptional silencing. In one aspect, cells whose genes have been silenced, e.g., transcriptionally silenced, include plant and animal cells. In one aspect, animal cells include fish cells.

Where appropriate, host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction).

Transgenic and Modified Fish

The invention provides genetically altered fish of the family Cyprinidae comprising at least one gene from a genetically altered gene or genes related to lipid metabolism, e.g., ApoE, ApoAI and/or LDL-R gene locus, wherein the fish can be of the family *Danio*, e.g., a zebrafish (*Danio rerio*). The transgenic animals can comprise a complete or partial gene or genes related to lipid metabolism, e.g., ApoE, ApoAI and/or LDL-R gene loci, or subsequences thereof, including an expression cassette or vector or a transfected or transformed cell comprising gene or genes related to lipid metabolism, e.g., a ApoE, ApoAI and/or LDL-R gene locus. The invention also provides methods of making and using these transgenic non-human animals.

"Knockout animals" can also be used to practice the methods of the invention. For example, in one aspect, the transgenic or modified fish of the invention comprise a "knockout animal," e.g., a "knockout" engineered not to express an endogenous gene, including any endogenous gene or genes related to lipid metabolism, e.g., the endogenous ApoE, ApoAI and/or LDL-R gene locus, or subsequences thereof. "Knockouts" can be prepared by deletion or disruption by homologous recombination of an endogenous promoter. "Knockout animals" or "Knockout cells" can be used to practice the methods of the invention. In one aspect, endogenous genes in stem cells are "knocked out" before insertion of a heterologous gene or genes related to lipid metabolism, e.g., ApoE, ApoAI and/or LDL-R gene locus, e.g., human or murine gene or genes related to lipid metabolism. In alternative aspects, stem cells are myeloid, lymphoid, or neural progenitor or precursor cells.

The invention also provides conditional transgenic or knockout fish produced using recombination methods. For example, an exemplary method comprises use of bacteriophage P1 Cre recombinase and flip recombinase from yeast plasmids. These are two non-limiting examples of site-specific DNA recombinase enzymes that cleave DNA at specific target sites (lox P sites for cre recombinase and frt. sites for flip recombinase) and catalyze a ligation of this DNA to a second cleaved site.

Any of the many known ways to modify the genetics (chromosomes, genes) of a fish can be used to make and practice the methods and compositions of the invention, e.g., inserting transgenes into the germ line of zebrafish. See, e.g., Linnet, et al., Dev Biol. 1999 Sep. 1; 213(1):207-16, "Transgene expression in zebrafish: A comparison of retroviral-vector and DNA-injection approaches" (transgenic fish that expressed a nuclear-targeted, enhanced, green fluorescent protein (EGFP) gene were produced using both pseudotyped retroviral vector infection and DNA microinjection of embryos); or, Sod, et al., Methods. 2006 July; 39(3):220-7, "Methods for reverse genetic screening in zebrafish by resequencing and TILLING" (using a reverse genetic approach that utilizes screening by resequencing and/or TILLING (Targeting Induced Local Lesions IN Genomes) of mutagenized genomes, spermatogonia of healthy males were mutagenized using ENU (N-ethyl-N-nitrosourea) and F1 progeny collected by breeding treated males with healthy wild type females); or, Wienholds, et al., Genome Res. 2003 December; 13(12):2700-7, "Efficient target-selected mutagenesis in zebrafish" (making a target-selected knockout in zebrafish using ENU-mutagenized F1 animals).

Drug Discovery

The methods and compositions of the invention can be used in drug discovery. The methods and compositions of the invention can be used for target validation; and, in some applications, can provide a physiologically accurate and less expensive approach to screen potential drugs. Expression arrays can be used to determine the expression of transgenic genes or genes other than a targeted gene or pathway.

The invention provides methods, cells and animals for determining the toxicity and pharmacokinetics of any compound, e.g., drugs, pesticides, herbicides, pollutants, and the like, using the cells and/or a fish of the invention.

Kits and Libraries

The invention provides kits comprising compositions and methods of the invention, including cells and/or fish of the invention, target sequences, transfecting agents, transducing agents, instructions (regarding the methods of the invention), or any combination thereof. As such, kits, cells, vectors and the like are provided herein.

The invention will be further described with reference to the following examples; however, it is to be understood that the invention is not limited to such examples.

EXAMPLES

Example 1

The invention provides an atherosclerosis model in which raising blood levels of cholesterol and other lipids in fish, e.g., zebrafish, leads to the cholesterol and other lipid accumulation in aorta and vascular inflammation.

Exemplary methods for making and using the invention are:

1. Cholesterol Feeding of Zebrafish

Spray cholesterol (4% in ether) on the fish food, let it dry for 2 hours in a fume hood. Collect and keep at 4° C. Feed the fish with high-cholesterol food for 7 days to 8 weeks.

Draw blood from adult zebrafish that was fed control or high-cholesterol diet and test the plasma for the levels of cholesterol, triglycerides and lipoprotein oxidation.

To visualize the lipid in larvae zebrafish, add to the cholesterol ether solution 10 μg/ml of cholesteryl BODIPY 576/589 C11 (Invitrogen, C12681). This fluorescent (red) cholesterol ester is almost exclusively carried in blood by LDL and does not translocate to other membranes, other than upon LDL cellular uptake. Feed fli:EGFP zebrafish with this high-cholesterol diet for one week.

Collect zebrafish blood and test for cholesterol content.

2. ApoE Knockdown

To knockdown ApoE, inject embryos with a morpholino antisense oligo. An ApoE specific morpholino has been designed and ordered from GeneTools:

```
apoeb-1    CAAAGAATACCACAAGAGACCTCAT  (SEQ ID NO: 9)
```

Test embryos for the ApoE expression using an anti-human ApoE antibody from Biodesign (K74180B, goat). This antibody has been demonstrated in our experiments to recognize a zebrafish protein of approximately the same size as human ApoE.

If ApoE knockdown leads to lipid and macrophage accumulation in the blood vessel wall in zebrafish, generate an ApoE knockout zebrafish.

3. Analysis of Vascular Inflammation and Atherosclerosis

Use a fluorescent confocal microscope to image dorsal aorta of a fli:EGFP zebrafish (wild type or ApoE knockdown) that was placed on a high-cholesterol diet, and compare with a control zebrafish that was fed a normal diet.

Visualize using a C1si confocal microscope:
endothelial cell morphology and the morphology of the vessel
accumulation of fluorescent lipid in the artery wall
Generate 3D rendered images of the aorta
Immunohistochemistry of the whole embryo/larva:
macrophages with Mac-3 antibody (BD Pharmingen)
oxidized lipid moieties with MDA-2 antibody (in-house)
phospho-Akt with a rabbit monoclonal antibody (Cell Signaling)
Hoechst 33258 to visualize cell nuclei Following immunohistochemical staining, image dorsal aorta in a whole fish with a confocal microscope. Then mount the fish, make cross sections and examine individual sections. Compare the 3D rendering from the confocal with the cross sections.

Harvest peritoneal macrophages from mice (ether wild type of genetically modified, e.g. 12/15-lipoxygenase deficient), fluorescently label them with CELLTRACKER™ (Invitrogen, Carlsbad, Calif.) and inject intraperitoneally into a zebrafish. Observe macrophage accumulation in the artery wall. This type of experiment will study the role of specific macrophage molecules in promoting inflammation in atherosclerotic lesions. Alternatively, human monocytes can be used for this purpose. Use nucleofection technology to achieve efficient monocyte transfection with either siRNA or transgene of interest.

Figure 1A:
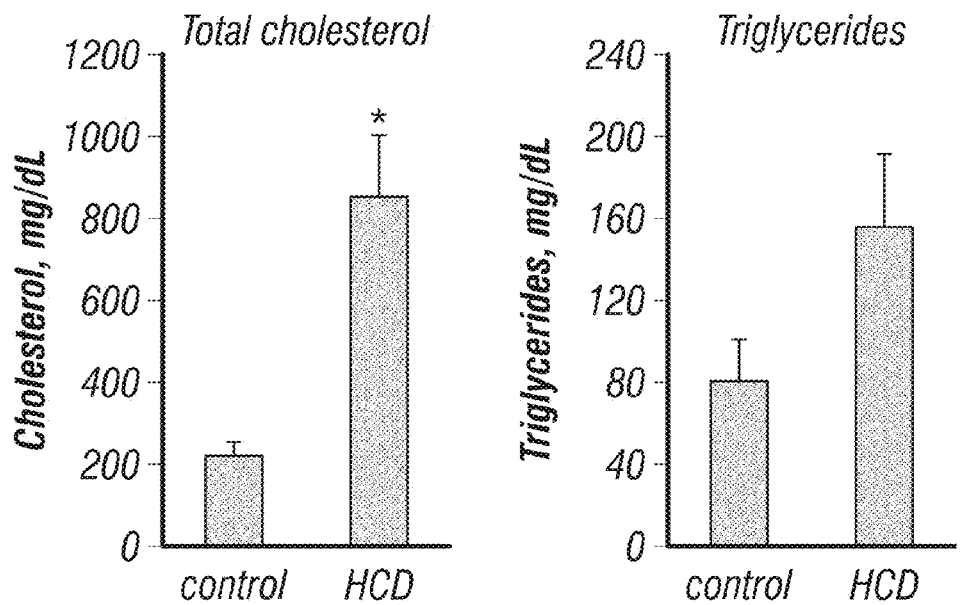
FIG. 1(A) illustrates data showing the total cholesterol (TC) and triglycerides (TG) in the plasma of a normal zebrafish and the zebrafish fed a high-cholesterol diet, as measured using automated enzymatic assays, as described in detail, below.
Figure 1B:
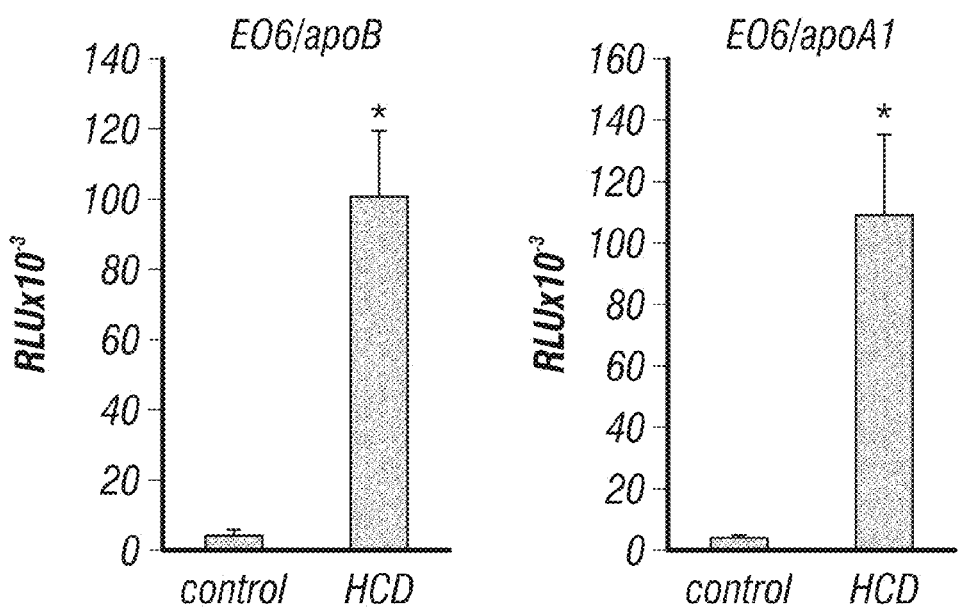
FIG. 1(B) illustrates data from an immunoassay used to detect oxidized phospholipids in LDL and in HDL in the plasma of a normal zebrafish and the zebrafish fed a high-cholesterol diet, as described in detail, below.

The following figures demonstrate the effectiveness of this invention: FIG. 1. Hypercholesterolemia and oxidized lipoproteins in adult zebrafish. Five week old zebrafish were fed a 4% cholesterol-enriched (HCD) or normal (control) diet, eight animals per group, for 8-10 weeks. Animals were euthanized by prolonged exposure to 0.02% Tricaine, and 2 μl blood was drawn from the heart and immediately diluted in 9 of ice-cold PBS-EDTA. After centrifugation, 1:10 diluted plasma was collected and used for analysis. FIG. 1 (A) Total cholesterol (TC) and triglycerides (TG) in plasma were measured using automated enzymatic assays. *, p<0.001. FIG. 1 (B) The EO6 immunoassay was used to detect oxidized phospholipids in LDL (EO6/apoB) and in HDL (EO6/apoA1). *, p<0.05. The increase in the EO6 reactivity 20-30 fold in the plasma of hyperlipidemic zebrafish is extremely and uniquely high compared to any animal model of atherosclerosis or human patient samples.

Figure 2:
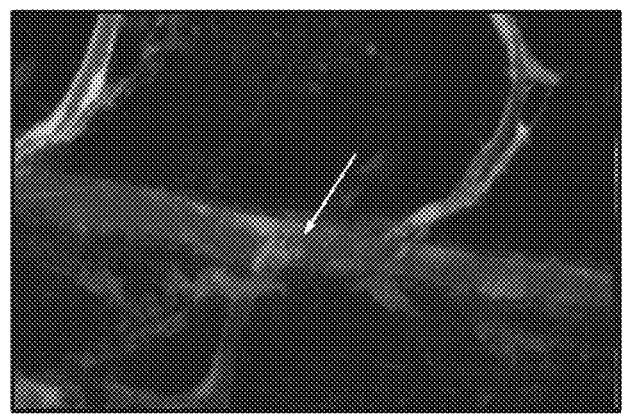
FIG. 2 illustrates a confocal microscope image of cholesterol accumulation in the vasculature of a zebrafish, as described in detail, below.

FIG. 2. Cholesterol accumulation in zebrafish arteries. Fli:EGFP zebrafish larvae were fed high-cholesterol diet, containing fluorescent (red) cholesterol ester for 7 days. A whole live zebrafish larva was placed under a confocal microscope and images of vasculature were captured. Green endothelial cells help trace blood vessels, which are also stained red due to a high content of cholesterol in blood. Note bright red areas of the artery (arrowhead), which indicate cholesterol accumulation in the artery wall.

FIG. 3. Disturbed endothelial cell morphology in the dorsal aorta of a fish fed high-cholesterol diet. Endothelial cells cover the inside surface of blood vessels and are first exposed to pro-inflammatory effects of the high cholesterol content in blood. Inflamed endothelium attracts leukocytes, which enter the blood vessel wall. These processes disturb endothelial cell morphology. In the fli:EGFP zebrafish strain, endothelial cells constitutively express EGFP, a fluorescent protein readily visualized with a confocal microscope. FIG. 3A and FIG. 3C are the images of dorsal aorta of a control and a high-cholesterol fed larva. Numerous "holes" (arrowhead) presumably are the sites of leukocytes attachment and entry through the endothelial cells.

Figure 3A:
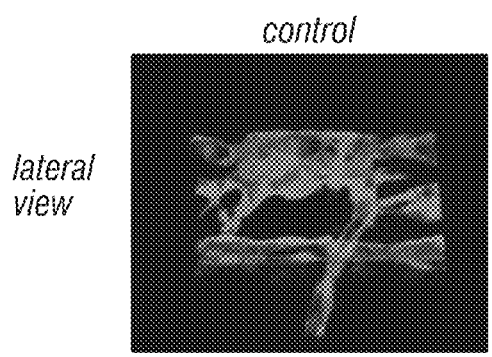
FIG. 3A and FIG. 3C are the images of dorsal aorta of a control and a high-cholesterol fed larva.
Figure 3C:
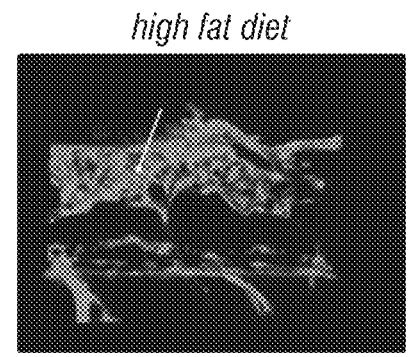
Figure 3B:
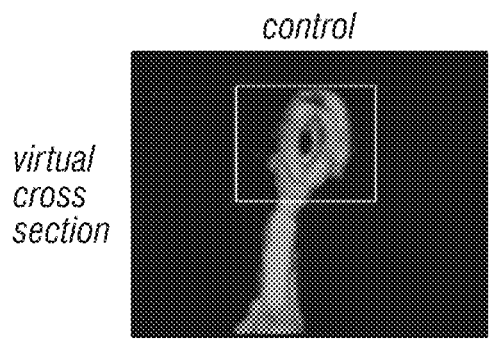
FIG. 3B and FIG. 3D are the 3D images of the same aorta segments.
Figure 3D:
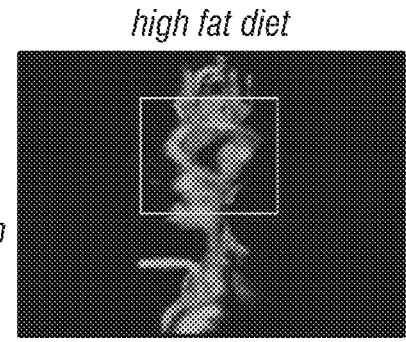
Figure 4A:
FIG. 4 illustrates a confocal microscope image of macrophage accumulation and cholesterol uptake in the dorsal aorta of a zebrafish larva, as described in detail, below.
Figure 4C:
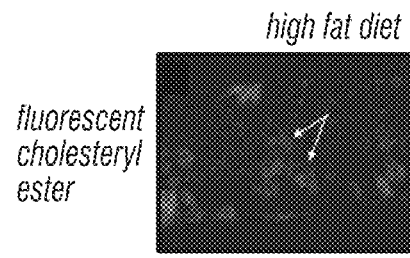
Figure 4B:
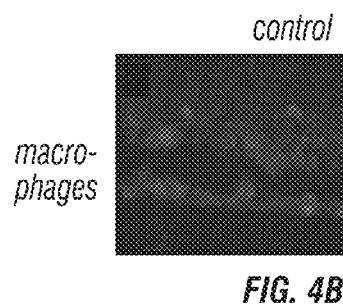
Figure 4D:
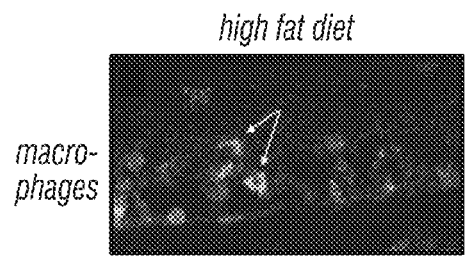

FIG. 3B and FIG. 3D are the 3D images of the same aorta segments, rendered from several optical sections through the aorta and rotated 90° to see the aorta lumen (highlighted). Irregular lumen morphology in the high-cholesterol fed zebrafish aorta (D) indicates endothelial cell activation and, possibly, leukocyte entry.

FIG. 4. Macrophage accumulation and cholesterol uptake in the dorsal aorta of a zebrafish larva. A zebrafish larva was euthanized following 7 days feeding on high fat diet with addition of a fluorescent (red) cholesterol ester. The whole larva was fixed and stained with Mac3 antibody (green). This antibody recognizes mouse macrophages and apparently crossreacts with zebrafish macrophages. Note that green macrophage staining colocalizes with the red cholesterol staining, indicating the uptake of the lipid by macrophages. The lipid-loaded macrophages are a hallmark of human and mouse atherosclerotic lesions.

Figure 5A:
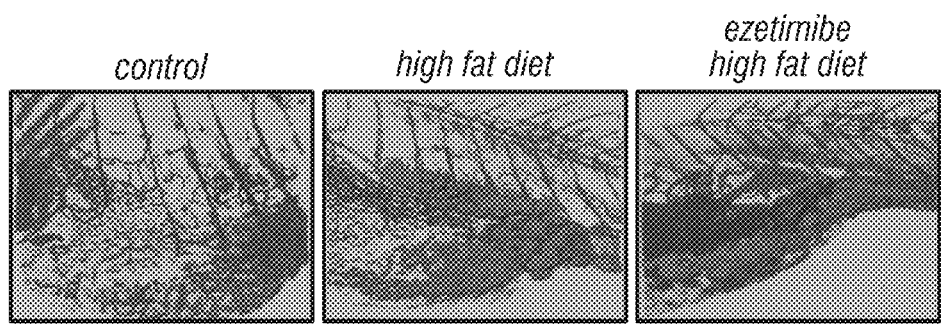
FIG. 5(A) illustrates a microscope image showing that the addition of ezetimibe in the fish tank water considerably reduced a level of cholesterol accumulated in the digestive system of a zebrafish; the FIG. 5(B) illustrates images that demonstrate that ezetimibe prevented pathological changes in the endothelial layer morphology of the zebrafish, as inflicted by a high fat diet, as described in detail, below.
Figure 5B:
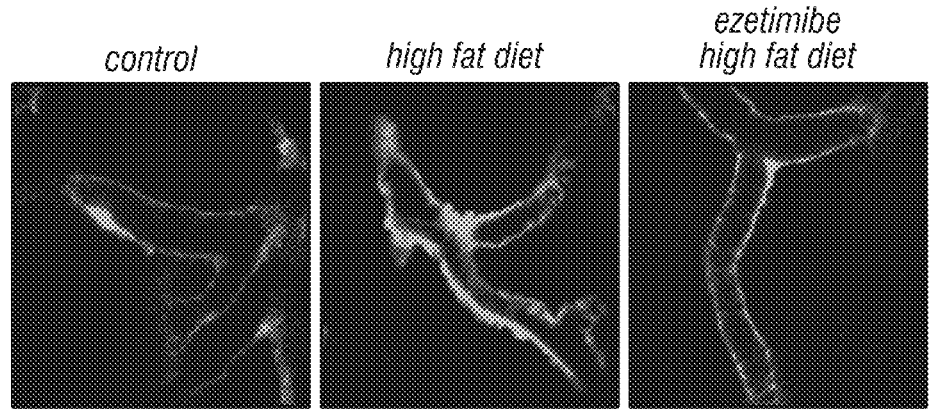
Figure 6:
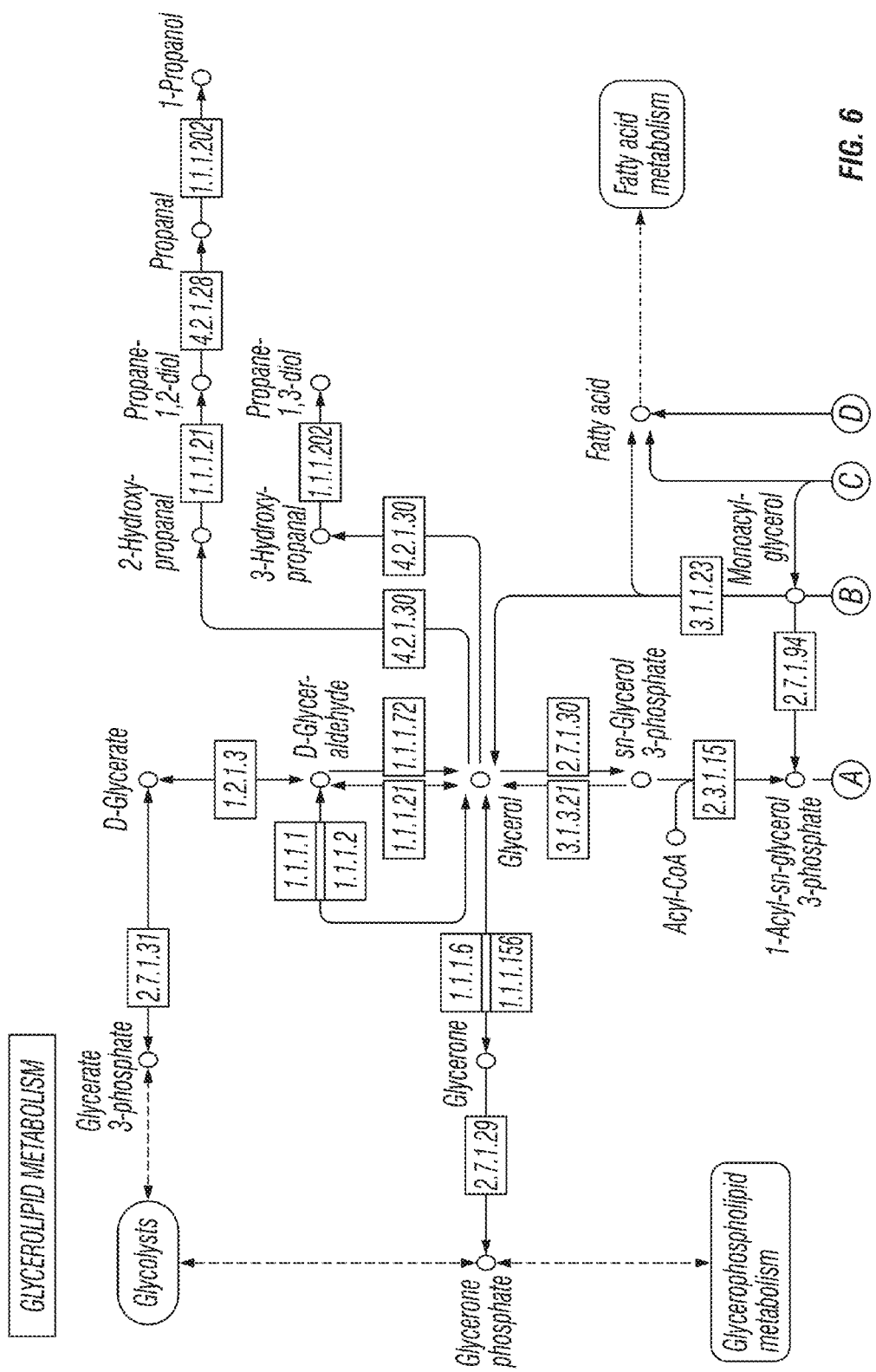
FIG. 6, FIG. 7 and FIG. 8 illustrate lipid-related metabolic pathways and their enzymes, including a glycerolipid metabolism pathway, a fatty acid biosynthesis pathway, and fatty acid metabolism, respectively, and set forth exemplary enzymes (including their fish homologues, or counterparts) that can be used to practice this invention.
Figure 6:
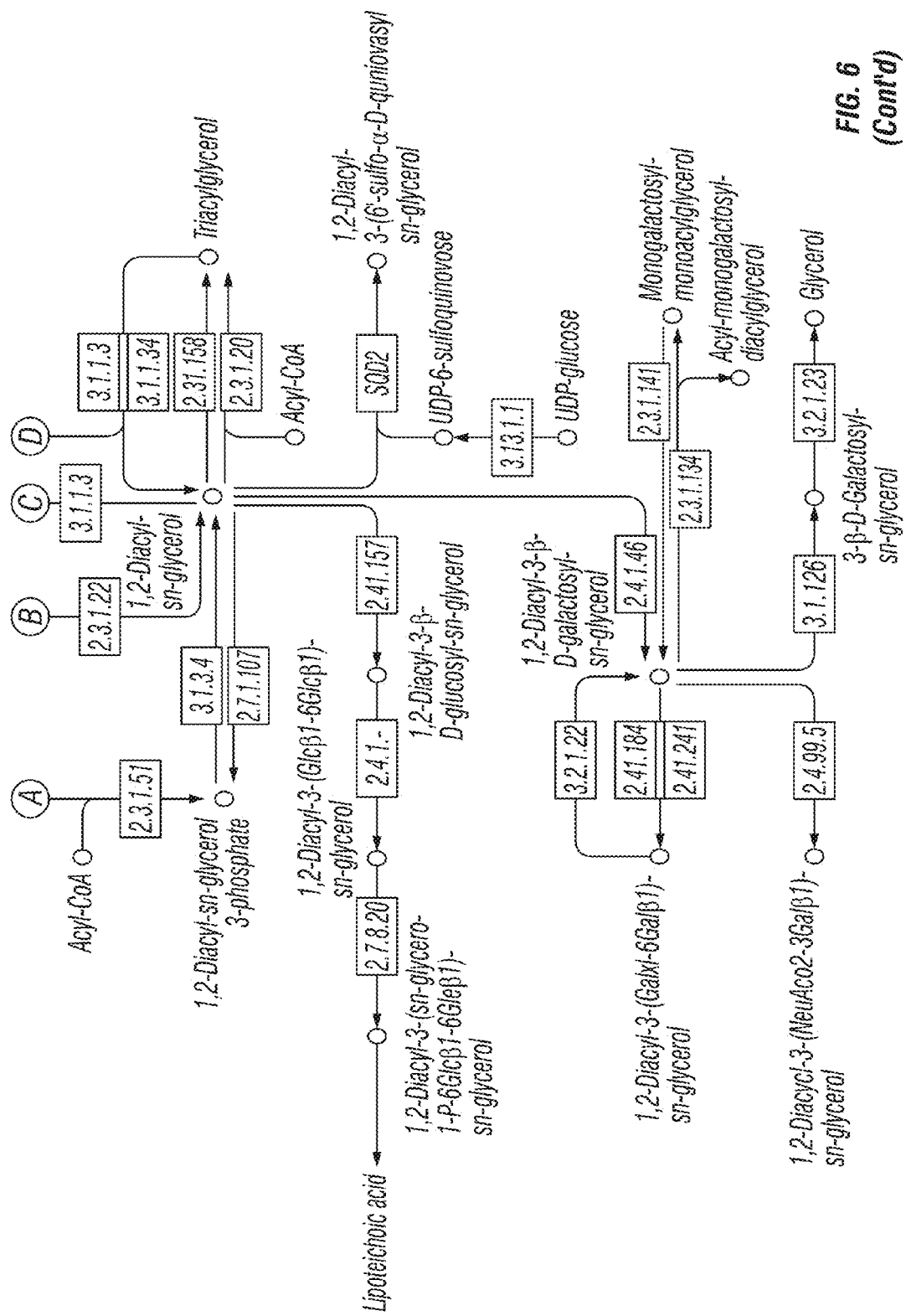
Figure 7:
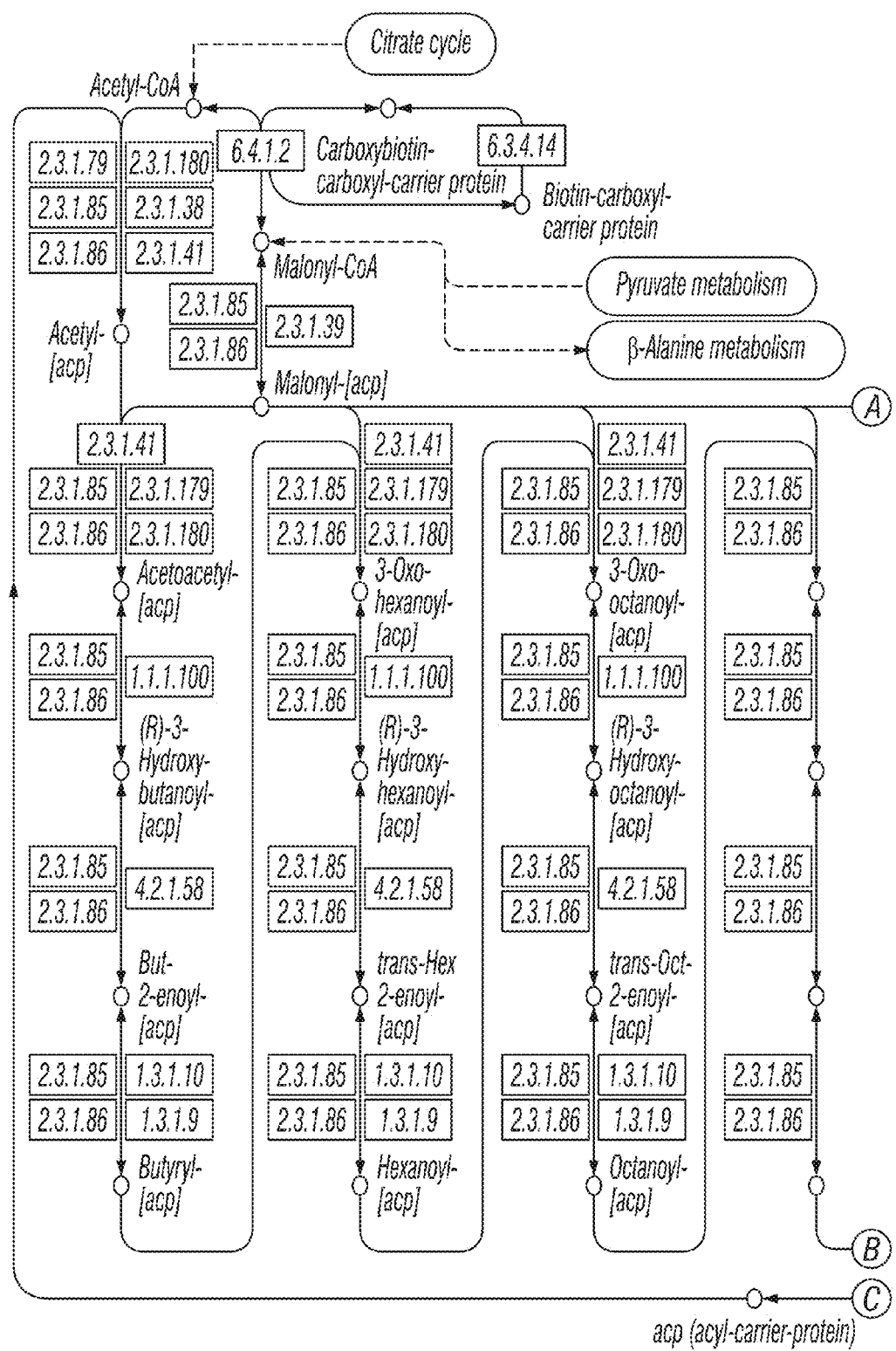
Figure 7:
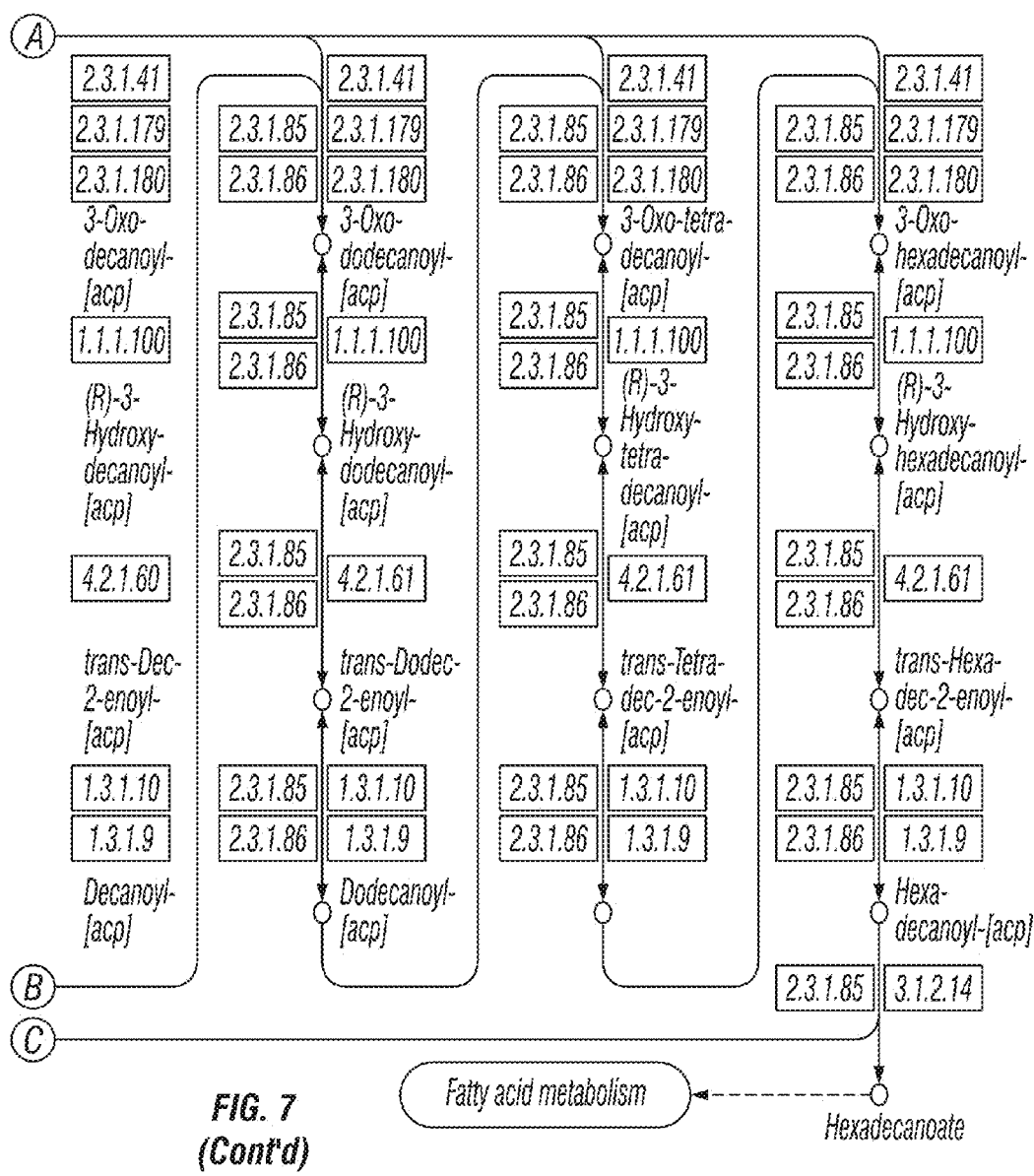
Figure 8:
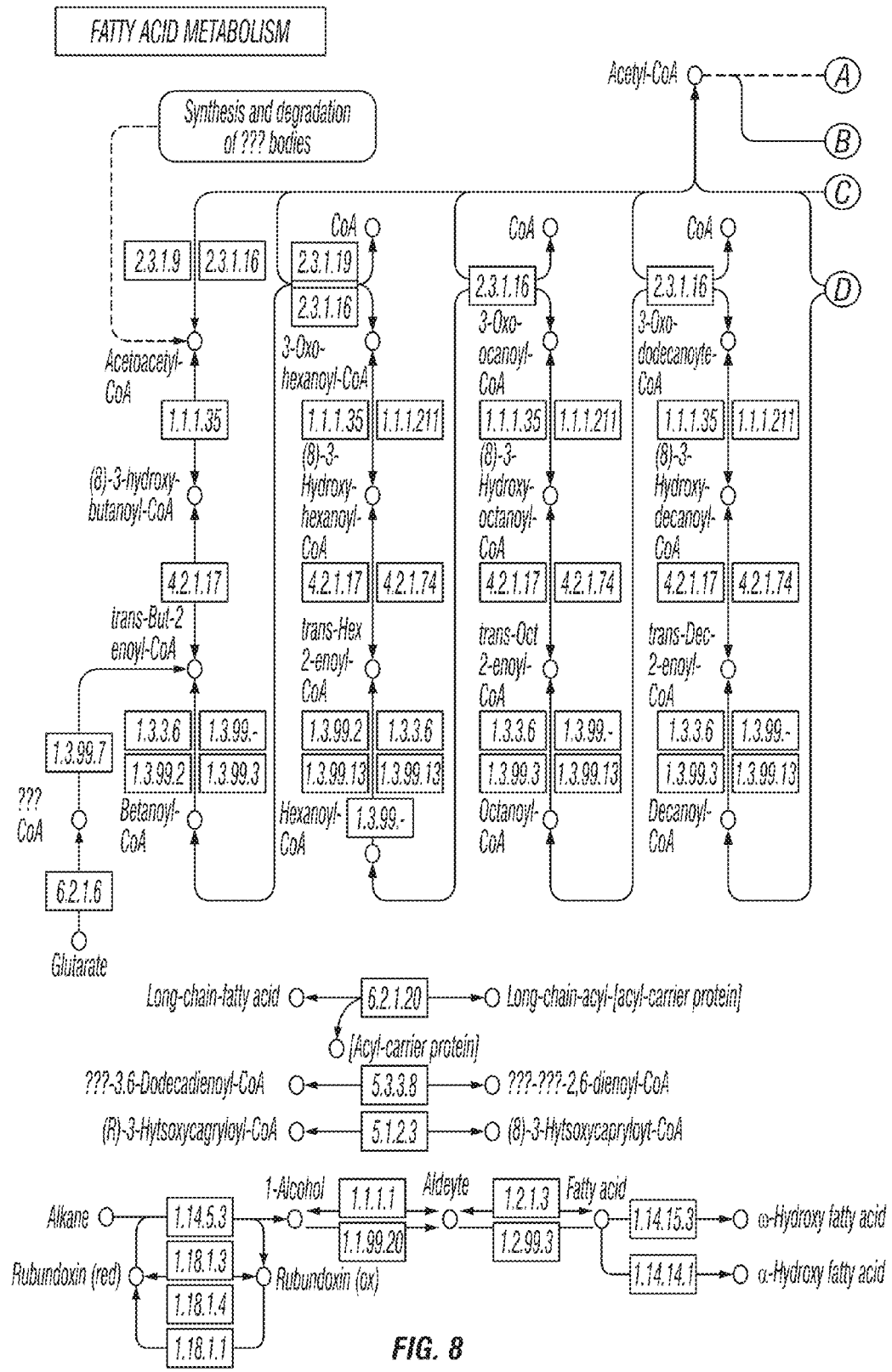
Figure 8:
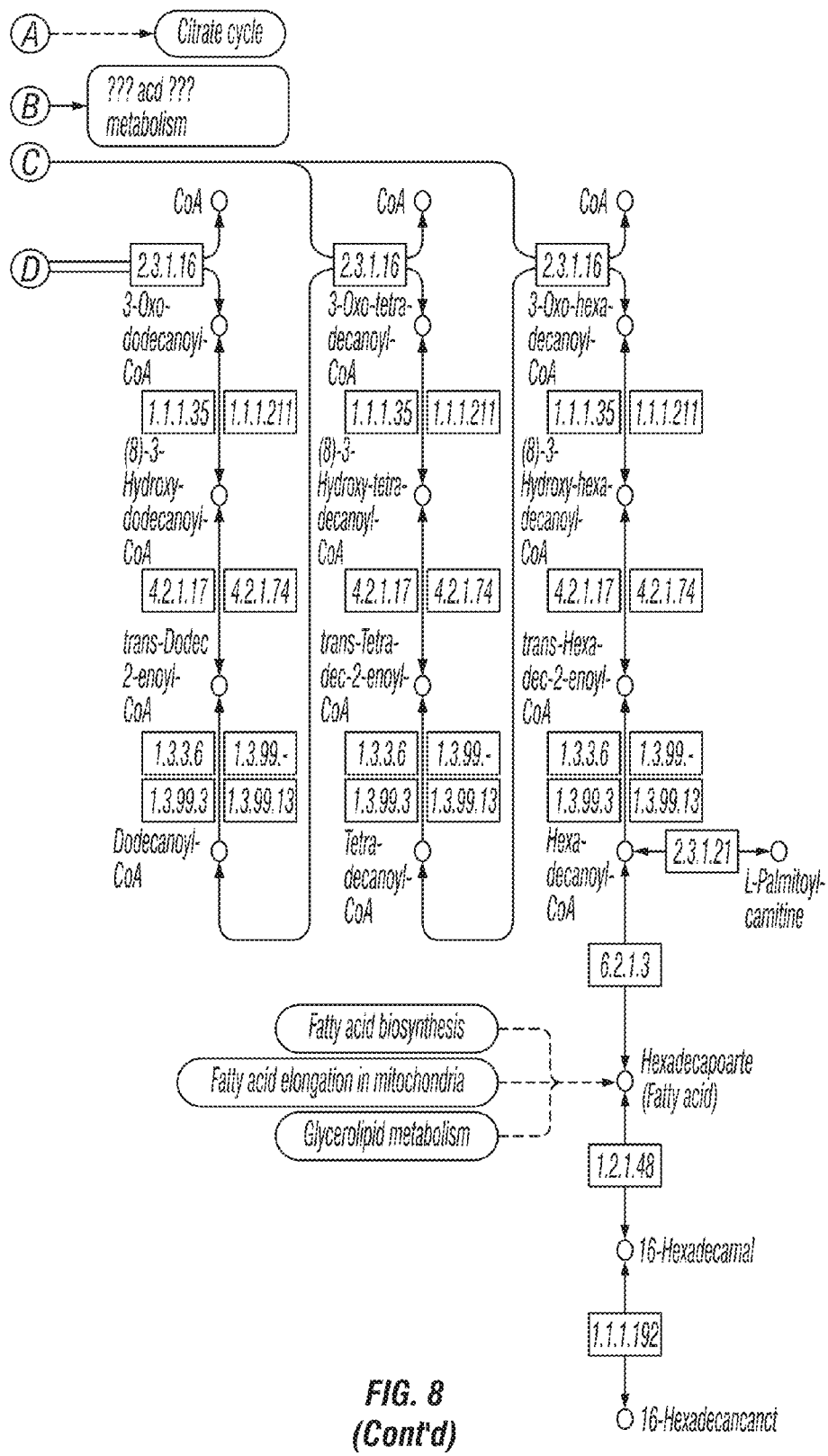

FIG. 5. Ezetimibe reduces cholesterol absorption in zebrafish intestine (A) and prevents vascular damage (B). Fli:EGFP zebrafish larvae were feeding for 10 days on high fat diet with a fluorescent (red) cholesterol ester, with or without the addition of ezetimibe in the tank water. Ezetimibe, or (3R,4S)-1-(4-fluorophenyl)-3-((3S)-3-(4-fluorophenyl)-3-hydroxypropyl)-4-(4-hydroxyphenyl)-2-azetidinone, is an FDA-approved medicine (marketed as ZETIA™), which inhibits the absorption of cholesterol by the small intestine. As is evident form the significant reduction in the intensity of red fluorescence (A), the addition of ezetimibe in the fish tank water considerably reduced a level of cholesterol accumulated in the digestive system of a zebrafish, which was fed a high fat diet. Remarkably, ezetimibe rescued blood vessels from high fat diet-induced damage. Images in panel B demonstrate that ezetimibe prevented pathological changes in the endothelial layer morphology, inflicted by high fat diet. These data serve as a prove of principal that our novel zebrafish model can be used to screen for drug candidates to prevent and/or stimulate regression of atherosclerotic vascular pathology.

These results demonstrate that the novel fish (e.g., zebrafish) models of the invention for atherosclerosis presents key characteristic features of the atherosclerotic process observed in humans; thus, the compositions, animals and methods of the invention provide highly informative and cost-effective screening of drug candidates for the treatment of atherosclerosis.

A number of embodiments of the invention have been described. Nevertheless, it will be understood that various modifications may be made without departing from the spirit and scope of the invention. Accordingly, other embodiments are within the scope of the following claims.

What is claimed is:

1. A method for screening for a compound capable of ameliorating or reversing:
   an atherosclerosis or
   a vascular inflammation associated with lipid accumulation in a blood vessel wall,
   the method comprising:
   (a) providing a test compound;
   (b) providing a genetically altered fish of the family Cyprinidae of the genus *Danio* having an induced vascular inflammation and atherosclerosis,
   wherein the vascular inflammation and atherosclerosis is induced by
      growing or subjecting the genetically altered *Danio* fish to an enriched cholesterol diet for a time sufficient to lead to cholesterol or lipid accumulation in an aorta and vascular inflammation,
   wherein the genetically altered *Danio* fish is a transgenic having an enhanced green fluorescence protein (EGFP) constitutively expressed in endothelial cells such that the *Danio* fish is optically transparent with a fluorescent vasculature (fli:EGFP), and the *Danio* fish has genetic alterations comprising knockdown of an ApoE, ApoAI and/or LDL-R gene locus;
   (c) administering the test compound to the genetically altered *Danio* fish of (b); and
   (d) determining if the test compound ameliorates or reverses the induced vascular inflammation or the atherosclerosis in the genetically altered *Danio* fish,
   wherein identifying a compound that can ameliorate or reverse the induced vascular inflammation or the atherosclerosis in the genetically altered *Danio* fish, identified the compound as a compound capable of ameliorating or reversing:
   an atherosclerosis or
   a vascular inflammation associated with lipid accumulation in a blood vessel wall.

2. The method of claim 1, wherein the enriched cholesterol diet further comprises a diet selected from the group consisting of:
   a high fat diet,
   an enriched fat diet,
   and
   a combination thereof.

3. The method of claim 1, wherein the test compound is selected from the group consisting of a small molecule, a polypeptide, a peptide, a nucleic acid, an siRNA, a polysaccharide, a lipid and a combination thereof.

4. The method of claim 1, wherein the test compound is designed to target and/or increase or decrease the activity of: a matrix metalloproteinase, a lipoxygenase, a cyclooxygenase, a phospholipase, a toll-like receptor, a NADPH oxidase, a nuclear receptor, a transcription factor NF-κB associated gene expression, or a combination thereof.

5. The method of claim 1, wherein the test compound is designed to target and/or increase or decrease: macrophage lipid uptake, endothelial adhesion molecules and/or monocyte recruitment, smooth muscle cell growth and migration, apoptosis of vascular cells, phagocytosis of apoptotic cells, activation of T- and B-1 cells in the lesions, or a combination thereof.

6. The method of claim 1, wherein the genetically altered *Danio* fish further comprises:
   (a) an expressed exogenous gene or an exogenous set of lipid metabolism genes;
   (b) a completely or partially deleted, or "knocked out" endogenous lipid metabolism gene or set of lipid metabolism genes; or
   (c) a combination of (a) and (b).

7. The method of claim 1, wherein the genetically altered *Danio* fish is a zebrafish (*Danio rerio*).

8. The method of claim 1, wherein in the genetically altered *Danio* fish the LDL-R gene or gene locus is completely knocked out.

9. The method of claim 1, wherein the ApoE, ApoAI and/or LDL-R gene locus has at least one nucleic acid residue altered or removed.

10. The method of claim 1, wherein the ApoE, ApoAI and/or LDL-R gene locus has an inserted heterologous sequence.

11. The method of claim 1, wherein the ApoE, ApoAI and/or LDL-R gene locus has a rearranged endogenous sequence.

12. The method of claim 1, wherein the ApoE, ApoAI and/or LDL-R gene locus is modified such that no amount or a less amount of ApoE, ApoAI and/or LDL-R message and/or polypeptide is expressed.

13. The method of claim 1, wherein in the ApoE, ApoAI and/or LDL-R gene locus is modified such that an ApoE, ApoAI and/or LDL-R polypeptide has no or less than wild type activity.

14. The method of claim 1, wherein the ApoE gene or gene locus is completely knocked out.

15. The method of claim 1, wherein in the ApoAI gene or gene locus is completely knocked out.

* * * * *

SEQUENCE LISTING

```
<160> NUMBER OF SEQ ID NOS: 9

<210> SEQ ID NO 1
<211> LENGTH: 1223
<212> TYPE: DNA
<213> ORGANISM: Homo sapiens

<400> SEQUENCE: 1
gggatccttg agtcctactc agccccagcg gaggtgaagg acgtccttcc ccaggagccg     60
actggccaat cacaggcagg aagatgaagg ttctgtgggc tgcgttgctg gtcacattcc    120
tggcaggatg ccaggccaag gtggagcaag cggtggagac agagccggag cccgagctgc    180
gccagcagac cgagtggcag agcggccagc gctgggaact ggcactgggt cgcttttggg    240
attacctgcg ctgggtgcag acactgtctg agcaggtgca ggaggagctg ctcagctccc    300
aggtcaccca ggaactgagg gcgctgatgg acgagaccat gaaggagttg aaggcctaca    360
aatcggaact ggaggaacaa ctgacccegg tggcggagga gacgcgggca cggctgtcca    420
```

```
aggagctgca ggcggcgcag gcccggctgg gcgcggacat ggaggacgtg tgcggccgcc    480
tggtgcagta ccgcggcgag gtgcaggcca tgctcggcca gagcaccgag gagctgcggg    540
tgcgcctcgc ctcccacctg cgcaagctgc gtaagcggct cctccgcgat gccgatgacc    600
tgcagaagcg cctggcagtg taccaggccg ggcccgcga gggcgccgag cgcggcctca    660
gcgccatccg cgagcgcctg ggcccctgg tggaacaggg ccgcgtgcgg gccgccactg    720
tgggctccct ggccggccag ccgctacagg agcgggccca ggcctggggc gagcggctgc    780
gcgcgcggat ggaggagatg ggcagccgga cccgcgaccg cctggacgag gtgaaggagc    840
aggtggcgga ggtgcgcgcc aagctggagg agcaggccca gcagatacgc ctgcaggccg    900
aggccttcca ggcccgcctc aagagctggt tcgagcccct ggtggaagac atgcagcgcc    960
agtgggccgg gctggtggag aaggtgcagg ctgccgtggg caccagcgcc gcccctgtgc   1020
ccagcgacaa tcactgaacg ccgaagcctg cagccatgcg accccacgcc accccgtgcc   1080
tcctgcctcc gcgcagcctg cagcgggaga ccctgtcccc gccccagccg tcctcctggg   1140 gtggaccta gtttaataaa gattcaccaa gtttcacgca aaaaaaaaa aaaaaaaaaa    1200 aaaaaaaaaa aaaaaaaaaa aaa                                           1223
```

<210> SEQ ID NO 2
<211> LENGTH: 317
<212> TYPE: PRT
<213> ORGANISM: Homo sapiens

<400> SEQUENCE: 2

```
Met Lys Val Leu Trp Ala Ala Leu Leu Val Thr Phe Leu Ala Gly Cys
 1               5                  10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
```

```
                 225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
                260                 265                 270

Glu Ala Phe Gln Ala Arg Leu Lys Ser Trp Phe Glu Pro Leu Val Glu
                275                 280                 285

Asp Met Gln Arg Gln Trp Ala Gly Leu Val Glu Lys Val Gln Ala Ala
        290                 295                 300

Val Gly Thr Ser Ala Ala Pro Val Pro Ser Asp Asn His
305                 310                 315

<210> SEQ ID NO 3
<211> LENGTH: 1345
<212> TYPE: DNA
<213> ORGANISM: Danio rerio

<400> SEQUENCE: 3
```

| | | | | | |
|---|---|---|---|---|---|
| atcaacatga | ggtctcttgt | ggtattcttt | gccctggcag | ttttaactgg | ctgccaggct | 60 |
| cgtagcctgt | tccaggctga | tgcccctcag | cccagatggg | aggagatggt | ggaccgtttc | 120 |
| tggcagtatg | tgtctgaact | caacacacaa | actgacggca | tggtgcaaaa | catcaagggc | 180 |
| tcccagctca | gcagagagct | tgacacacta | attactgaca | ccatggctga | actgagctca | 240 |
| tacagtgaaa | atctccaaac | ccagatgacc | ccatatgcct | ctgatgctgc | tggtcagctc | 300 |
| agtaaagatc | ttcagctcct | ggctggaaaa | ctccaaactg | acatgaccga | cgctaaggaa | 360 |
| cgcagcactc | agtacctgca | agagctgaag | accatgatgg | agcaaaatgc | agatgacgtg | 420 |
| aagaaccgtg | tcggcaccta | cacgcgcaaa | ctgaagaaac | gcctgaacaa | ggacacagag | 480 |
| gagatccgca | acaccgtagc | aacctacatg | agtgagatgc | agtcccgcgc | ttcccaaaat | 540 |
| gctgatgcag | tgaaggaccg | tttccagcca | tacatgagcc | aggcccagga | tggcgccacc | 600 |
| cagaaactgg | gcgccattag | cgagctgatg | aaggcccagg | cgcaggaggt | gagcgagcag | 660 |
| ttggaggtcc | aggctggagc | tctgaaggag | aagctggagg | agacagccga | gaacctacgc | 720 |
| acctctctgg | agggccgtgt | ggatgagctg | accagcctcc | tcgcccccta | ctcccagaag | 780 |
| atccgcgagc | agctgcagga | agtcatggac | aagatcaagg | aggccacagc | agctcttccc | 840 |
| actcaggctt | aagagctcca | cacttaccta | gtgttaacac | caaacagaaa | gaagaaggga | 900 |
| ggctttgtgt | tactgaaatg | tgcttttttc | attctgtgag | aggttgataa | agtggttaac | 960 |
| aactggactc | aattggacta | gcactgtcct | ttactggaca | aaagaaatgc | catgttactc | 1020 |
| accacgttta | ctttctcagt | attaacccat | gtctgaggat | atatttctgt | tagcgtacag | 1080 |
| tagagcgaat | ttaagatcaa | tcaacttgtc | tgtcttggag | gctattttt | ctagttagtg | 1140 |
| gggccaaact | tggcgtcatt | caaaataaat | agtaatcaaa | aggtgccttc | agctgctgaa | 1200 |
| atgaatcaga | acacatgaaa | gatgagcttt | gttagtcaac | agtccacata | taatgcttg | 1260 |
| tttactttac | atgtttgtgc | actgatgtgt | ttgaatttgt | ttgcaataaa | tgtgcgttct | 1320 |
| actacacaaa | aaaaaaaaaa | aaaaa | | | | 1345 |

```
<210> SEQ ID NO 4
<211> LENGTH: 281
<212> TYPE: PRT
<213> ORGANISM: Danio rerio

<400> SEQUENCE: 4
```

```
Met Arg Ser Leu Val Phe Phe Ala Leu Ala Val Leu Thr Gly Cys
1               5                   10                  15

Gln Ala Arg Ser Leu Phe Gln Ala Asp Ala Pro Gln Pro Arg Trp Glu
            20                  25                  30

Glu Met Val Asp Arg Phe Trp Gln Tyr Val Ser Glu Leu Asn Thr Gln
        35                  40                  45

Thr Asp Gly Met Val Gln Asn Ile Lys Gly Ser Gln Leu Ser Arg Glu
    50                  55                  60

Leu Asp Thr Leu Ile Thr Asp Thr Met Ala Glu Leu Ser Ser Tyr Ser
65                  70                  75                  80

Glu Asn Leu Gln Thr Gln Met Thr Pro Tyr Ala Ser Asp Ala Ala Gly
            85                  90                  95

Gln Leu Ser Lys Asp Leu Gln Leu Leu Ala Gly Lys Leu Gln Thr Asp
            100                 105                 110

Met Thr Asp Ala Lys Glu Arg Ser Thr Gln Tyr Leu Gln Glu Leu Lys
            115                 120                 125

Thr Met Met Glu Gln Asn Ala Asp Asp Val Lys Asn Arg Val Gly Thr
130                 135                 140

Tyr Thr Arg Lys Leu Lys Lys Arg Leu Asn Lys Asp Thr Glu Ile
145                 150                 155                 160

Arg Asn Thr Val Ala Thr Tyr Met Ser Glu Met Gln Ser Arg Ala Ser
                165                 170                 175

Gln Asn Ala Asp Ala Val Lys Asp Arg Phe Gln Pro Tyr Met Ser Gln
            180                 185                 190

Ala Gln Asp Gly Ala Thr Gln Lys Leu Gly Ala Ile Ser Glu Leu Met
            195                 200                 205

Lys Ala Gln Ala Gln Glu Val Ser Glu Gln Leu Glu Val Gln Ala Gly
            210                 215                 220

Ala Leu Lys Glu Lys Leu Glu Glu Thr Ala Glu Asn Leu Arg Thr Ser
225                 230                 235                 240

Leu Glu Gly Arg Val Asp Glu Leu Thr Ser Leu Leu Ala Pro Tyr Ser
                245                 250                 255

Gln Lys Ile Arg Glu Gln Leu Glu Val Met Asp Lys Ile Lys Glu
            260                 265                 270

Ala Thr Ala Ala Leu Pro Thr Gln Ala
            275                 280
```

<210> SEQ ID NO 5
<211> LENGTH: 897
<212> TYPE: DNA
<213> ORGANISM: Homo sapiens

<400> SEQUENCE: 5

```
agagactgcg agaaggaggt cccccacggc ccttcaggat gaaagctgcg gtgctgacct      60
tggccgtgct cttcctgacg gggagccagg ctcggcattt ctggcagcaa gatgaacccc    120
cccagagccc ctgggatcga gtgaaggacc tggccactgt gtacgtggat gtgctcaaag    180
acagcggcag agactatgtg tcccagtttg aaggctccgc cttgggaaaa cagctaaacc    240
taaagctcct tgacaactgg gacagcgtga cctccacctt cagcaagctg cgcgaacagc    300
tcggccctgt gacccaggag ttctgggata acctggaaaa ggagacagag ggcctgaggc    360
aggagatgag caaggatctg agggaggtga aggccaaggt gcagccctac ctggacgact    420
tccagaagaa gtggcaggag gagatggagc tctaccgcca gaaggtggag ccgctgcgcg    480
cagagctcca gagggcgcg cgccagaagc tgcacgagct gcaagagaag ctgagcccac    540
```

```
tgggcgagga gatgcgcgac cgcgcgcgcg cccatgtgga cgcgctgcgc acgcatctgg    600 cccctacag cgacgagctg cgccagcgct tggccgcgcg ccttgaggct ctcaaggaga      660
acggcggcgc cagactggcc gagtaccacg ccaaggccac cgagcatctg agcacgctca    720
gcgagaaggc caagcccgcg ctcgaggacc tccgccaagg cctgctgccc gtgctggaga    780
gcttcaaggt cagcttcctg agcgctctcg aggagtacac taagaagctc aacacccagt    840
gaggcgcccg ccgccgcccc ccttcccggt gctcagaata aacgtttcca aagtggg        897
```

<210> SEQ ID NO 6
<211> LENGTH: 267
<212> TYPE: PRT
<213> ORGANISM: Homo sapiens

<400> SEQUENCE: 6

```
Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265
```

<210> SEQ ID NO 7
<211> LENGTH: 2600
<212> TYPE: DNA
<213> ORGANISM: Homo sapiens

<400> SEQUENCE: 7

-continued

```
cagaggctgc gagcatgggg ccctgggget ggaaattgcg ctggaccgtc gccttgctcc       60
tcgccgcggc ggggactgca gtgggcgaca gatgcgaaag aaacgagttc cagtgccaag      120
acgggaaatg catctcctac aagtgggtct gcgatggcag cgctgagtgc caggatggct      180
ctgatgagtc ccaggagacg tgcttgtctg tcacctgcaa atccggggac ttcagctgtg      240
ggggccgtgt caaccgctgc attcctcagt tctggaggtg cgatggccaa gtggactgcg      300
acaacggctc agacgagcaa ggctgtcccc caagacgtg ctcccaggac gagtttcgct       360
gccacgatgg gaagtgcatc tctcggcagt tcgtctgtga ctcagaccgg gactgcttgg      420
acggctcaga cgaggcctcc tgcccggtgc tcacctgtgg tcccgccagc ttccagtgca      480
acagctccac ctgcatcccc cagctgtggg cctgcgacaa cgaccccgac tgcgaagatg      540
gctcggatga gtgccgcag cgctgtaggg gtctttacgt gttccaaggg gacagtagcc       600
cctgctcggc cttcgagttc cactgcctaa gtggcgagtg catccactcc agctggcgct      660
gtgatggtgg ccccgactgc aaggacaaat ctgacgagga aaactgcgct gtggccacct      720
gtcgccctga cgaattccag tgctctgatg aaactgcat ccatggcagc cggcagtgtg       780
accgggaata tgactgcaag gacatgagcg atgaagttgg ctgcgttaat gtgacactct      840
gcgagggacc caacaagttc aagtgtcaca gcggcgaatg catcaccctg gacaaagtct      900
gcaacatggc tagagactgc cgggactggt cagatgaacc catcaaagag tgcgggacca      960
acgaatgctt ggacaacaac ggcggctgtt cccacgtctg caatgacctt aagatcggct     1020
acgagtgcct gtgccccgac ggcttccagc tggtggccca gcgaagatgc gaagatatcg     1080
atgagtgtca ggatcccgac acctgcagcc agctctgcgt gaacctggag ggtggctaca     1140
agtgccagtg tgaggaaggc ttccagctgg acccccacac gaaggcctgc aaggctgtgg     1200
gctccatcgc ctacctcttc ttcaccaacc ggcacgaggt caggaagatg acgctggacc     1260
ggagcgagta caccagcctc atccccaacc tgaggaacgt ggtcgctctg gacacggagg     1320
tggccagcaa tagaatctac tggtctgacc tgtcccagag aatgatctgc agcacccagc     1380
ttgacagagc ccacggcgtc tcttcctatg acaccgtcat cagcagggac atccaggccc     1440
ccgacgggct ggctgtggac tggatccaca gcaacatcta ctggaccgac tctgtcctgg     1500
gcactgtctc tgttgcggat accaagggcg tgaagaggaa aacgttattc agggagaacg     1560
gctccaagcc aagggccatc gtggtggatc ctgttcatgg cttcatgtac tggactgact     1620
ggggaactcc cgccaagatc aagaagggg gcctgaatgg tgtggacatc tactcgctgg     1680
tgactgaaaa cattcagtgg cccaatgca tcaccctaga tctcctcagt ggccgcctct      1740
actgggttga ctccaaactt cactccatct caagcatcga tgtcaacggg gcaaccgga     1800
agaccatctt ggaggatgaa aagaggctgg cccaccctt tccttggcc gtctttgagg       1860
acaaagtatt ttggacagat atcatcaacg aagccatttt cagtgccaac cgcctcacag     1920
gttccgatgt caacttgttg gctgaaaacc tactgtcccc agaggatatg gttctcttcc     1980
acaacctcac ccagccaaga ggagtgaact ggtgtgagag gaccaccctg agcaatggcg     2040
gctgccagta tctgtgcctc cctgccccgc agatcaaccc ccactcgccc aagtttacct     2100
gcgcctgccc ggacggcatg ctgctggcca gggacatgag gagctgcctc acagaggctg     2160
aggctgcagt ggccacccag gagacatcca ccgtcaggct aaaggtcagc tccacagccg     2220
taaggacaca gcacacaacc acccggcctg ttcccgacac ctcccggctg cctggggcca     2280
cccctgggct caccacggtg gagatagtga caatgtctca ccaagctctg ggcgacgttg     2340
```

-continued

```
ctggcagagg aaatgagaag aagcccagta gcgtgagggc tctgtccatt gtcctcccca   2400
tcgtgctcct cgtcttcctt tgcctggggg tcttccttct atggaagaac tggcggctta   2460
agaacatcaa cagcatcaac tttgacaacc ccgtctatca gaagaccaca gaggatgagg   2520
tccacatttg ccacaaccag gacggctaca gctacccctc gagacagatg gtcagtctgg   2580
aggatgacgt ggcgtgaaca                                                 2600

<210> SEQ ID NO 8
<211> LENGTH: 860
<212> TYPE: PRT
<213> ORGANISM: Homo sapiens

<400> SEQUENCE: 8

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
        275                 280                 285

Cys Ile Thr Leu Asp Lys Val Cys Asn Met Ala Arg Asp Cys Arg Asp
    290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
```

-continued

```
                325                 330                 335
Glu Cys Leu Cys Pro Asp Gly Phe Gln Leu Val Ala Gln Arg Arg Cys
                340                 345                 350

Glu Asp Ile Asp Glu Cys Gln Asp Pro Asp Thr Cys Ser Gln Leu Cys
                355                 360                 365

Val Asn Leu Glu Gly Gly Tyr Lys Cys Gln Cys Glu Gly Phe Gln
                370             375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
                420                 425                 430

Asp Thr Glu Val Ala Ser Asn Arg Ile Tyr Trp Ser Asp Leu Ser Gln
                435                 440                 445

Arg Met Ile Cys Ser Thr Gln Leu Asp Arg Ala His Gly Val Ser Ser
                450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
                500                 505                 510

Arg Glu Asn Gly Ser Lys Pro Arg Ala Ile Val Val Asp Pro Val His
                515                 520                 525

Gly Phe Met Tyr Trp Thr Asp Trp Gly Thr Pro Ala Lys Ile Lys Lys
                530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
                580                 585                 590

Gly Asn Arg Lys Thr Ile Leu Glu Asp Glu Lys Arg Leu Ala His Pro
                595                 600                 605

Phe Ser Leu Ala Val Phe Glu Asp Lys Val Phe Trp Thr Asp Ile Ile
                610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
                660                 665                 670

Ser Asn Gly Gly Cys Gln Tyr Leu Cys Leu Pro Ala Pro Gln Ile Asn
                675                 680                 685

Pro His Ser Pro Lys Phe Thr Cys Ala Cys Pro Asp Gly Met Leu Leu
                690                 695                 700

Ala Arg Asp Met Arg Ser Cys Leu Thr Glu Ala Glu Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
                740                 745                 750
```

```
Pro Gly Ala Thr Pro Gly Leu Thr Thr Val Glu Ile Val Thr Met Ser
        755             760             765

His Gln Ala Leu Gly Asp Val Ala Gly Arg Gly Asn Glu Lys Lys Pro
        770             775             780

Ser Ser Val Arg Ala Leu Ser Ile Val Leu Pro Ile Val Leu Leu Val
785             790             795                     800

Phe Leu Cys Leu Gly Val Phe Leu Leu Trp Lys Asn Trp Arg Leu Lys
                805             810                 815

Asn Ile Asn Ser Ile Asn Phe Asp Asn Pro Val Tyr Gln Lys Thr Thr
                820             825             830

Glu Asp Glu Val His Ile Cys His Asn Gln Asp Gly Tyr Ser Tyr Pro
        835             840             845

Ser Arg Gln Met Val Ser Leu Glu Asp Asp Val Ala
        850             855             860

<210> SEQ ID NO 9
<211> LENGTH: 25
<212> TYPE: DNA
<213> ORGANISM: artificial sequence
<220> FEATURE:
<223> OTHER INFORMATION: antisense oligonucleotide

<400> SEQUENCE: 9
caaagaatac cacaagagac ctcat                                                25
```